United States Patent [19]

Jaskunas

[11] Patent Number: 4,874,703
[45] Date of Patent: Oct. 17, 1989

[54] **EXPRESSION VECTORS FOR USE IN *E. COLI***

[75] Inventor: S. Richard Jaskunas, Indianapolis, Ind.

[73] Assignee: Eli Lilly and Company, Indianapolis, Ind.

[21] Appl. No.: 769,221

[22] Filed: Aug. 26, 1985

[51] Int. Cl.[4] .................. C12N 15/00; C12N 1/20; C07H 15/12; C12P 1/04
[52] U.S. Cl. .................. 435/252.33; 435/320; 435/170; 435/849; 435/172.3; 536/27; 935/8; 935/29; 935/41; 935/42; 935/43; 935/45; 935/47; 935/61; 935/73
[58] Field of Search .................. 536/27; 435/68, 91, 435/170, 172.3, 252.3, 252.33, 320, 849; 935/8, 29, 41, 42, 43, 45, 47, 61, 73

[56] References Cited

U.S. PATENT DOCUMENTS

| | | | |
|---|---|---|---|
| 4,363,877 | 12/1982 | Goodman et al. | 435/317 |
| 4,643,969 | 2/1987 | Inouye et al. | 435/68 |
| 4,745,069 | 5/1988 | Mayne et al. | 435/320 |

FOREIGN PATENT DOCUMENTS

84107717.5  3/1984  European Pat. Off. .

OTHER PUBLICATIONS

Waldman et al. 1983 J. Biol Chemistry, (19): 11571-11575.
Cesaremi et al. 1982. Proc. Natl. Acad. Sci USA 80:3232.
Simons et al. 1984. Gene 28:55.
Kuhstoss & Rao, 1982, Abstract of Poster Presentation at the 13th Intnl. Congress of Microbiology in Boston, MA
Derynck et al., 1980, Nature 287:193.
Shimatake and Rosenberg, 1981, Nature 292:128.
Remaut et al., 1981, Gene 15:81.
Derom et al., 1982, Gene 17:45.
Simons et al., 1984, Gene 28:55.

*Primary Examiner*—Thomas G. Wiseman
*Assistant Examiner*—Richard C. Peet
*Attorney, Agent, or Firm*—Ron K. Levy; Leroy Whitaker

[57] ABSTRACT

The present invention provides a transcriptional and translational activating sequence derived from the lambda pL transcriptional activating sequence and the *E. coli* lpp translational activating sequence. The activating sequence has been cloned into recombinant DNA expression vectors into which DNA sequences encoding funtional polypeptides can be readily inserted and expressed. The activating sequence of the present invention has been shown to drive high-level expression of a bovine growth hormone derivative and a human growth hormone derivative in *E. coli*. Preferred expression vectors of the present invention also comprise the cI857 temperature-sensitive lambda pL repressor gene, a rop⁻ derivative of the plasmid pBR322 replicon, and a tetracycline resistance-conferring gene.

24 Claims, 14 Drawing Sheets

Restriction Site and Function Map of Plasmid pKC283
(9.1 kb)

Restriction Site and Function Map of Plasmid pKC283PX
(6.1 kb)

Restriction Site and Function Map of Plasmid pKC283-L
(5.9 kb)

Restriction Site and Function Map of Plasmid pKC283-LB
(5.9 kb)

Restriction Site and Function Map of Plasmid pKC283PRS
(4.0 kb)

Restriction Site and Function Map of Plasmid pL32
(3.9 kb)

Restriction Site and Function Map of Plasmid pL47
(4.5 kb)

Restriction Site and Function Map of Plasmid pL84
(5.5 kb)

Restriction Site and Function Map of Plasmid pL95
(3.8 kb)

Restriction Site and Function Map of Plasmid pPR12
(5.1 kb)

Restriction Site and Function Map of Plasmid pPR12AR1
(5.1 kb)

Restriction Site and Function Map of Plasmid pL110
(6.6 kb)

Restriction Site and Function Map of Plasmid pL111
(6.0 kb)

Restriction Site and Function Map of Plasmid pCC101
(10.8 kb)

EXPRESSION VECTORS FOR USE IN E. COLI

SUMMARY OF THE INVENTION

The present invention provides a novel transcriptional and translational activating sequence and related recombinant DNA expression vectors for use in *E. coli*. The novel activating sequence is derived from the bacteriophage lambda pL promoter and the *E. coli* lpp gene translational activating sequence. The preferred expression vectors of the present invention utilize the novel transcriptional and translational activating sequence of the present invention, the temperature-sensitive lambda cI repressor gene cI857, a tetracycline resistance-conferring gene, and a rop⁻ derivative of the replicon of plasmid pBR322.

The expression vectors of the present invention are versatile and allow expression of any functional polypeptide-encoding gene of interest, provided that the gene is introduced into the vector in the correct reading phase. The utility and versatility of the present expression vectors are exemplified by plasmids disclosed herein that, when introduced into *E. coli* and the resulting transformants cultured at the appropriate temperature, drive expression of a bovine growth hormone derivative or a human growth hormone derivative to levels approaching 30% of the total cellular protein.

For purposes of the present invention, as disclosed and claimed herein, the following terms are as defined below.

Amino acid residues are abbreviated as follows:
ALA is an Alanine
ARG is an Arginine
ASN is an Asparagine
ASP is an Aspartic
CYS is a Cysteine
GLN is a Glutamine
GLU is a Glutamic Acid
GLY is a Glycine
HIS is a Histidine
ILE is an Isoleucine
LEU is a Leucine
LYS is a Lysine
MET is a Methionine
PHE is a Phenylalanine
PRO is a Proline
SER is a Serine
THR is a Threonine
TRP is a Tryptophan
TYR is a Tyrosine
VAL is a Valine Antibiotic—a substance produced by a microorganism that either naturally or with limited chemical modification will inhibit the growth of or kill another microorganism or eukaryotic cell.

Antibiotic Resistance-Conferring Gene—a DNA segment that encodes an enzymatic or other activity which confers resistance to an antibiotic.

ApR—the ampicillin-resistant phenotype or gene conferring the same.

Cloning—the process of incorporating a segment of DNA into a recombinant DNA cloning or expression vector.

Deoxyribonucleotide residues are abbreviated as follows:
A is deoxyadenyl;
G is deoxyguanyl;
C is deoxycytidyl; and
T is thymidyl.

EK-BGH—methionyl-phenylalanyl-leucinyl(aspartyl)₄-lysinyl-bovine growth hormone, which is bovine growth hormone, beginning with the amino-terminal phenylalanyl residue, linked at the amino-terminus to amino acid residues that encode an enterokinase cleavage site. On the plasmid maps herein, the gene that encodes such a bovine growth hormone derivative is represented as EK-BGH.

Functional Polypeptide—a recoverable bioactive entirely heterologous or homologous polypeptide or precursor, a recoverable bioactive polypeptide comprising a heterologous polypeptide and a portion or whole of a homologous polypeptide or a recoverable bioinactive fusion polypeptide comprising a heterologous polypeptide and a bioinactivating homologous polypeptide that can be specifically cleaved.

KmR—the kanamycin-resistant phenotype or gene conferring the same.

lppT—the transcription terminator sequence of the *E. coli* lpp gene.

MET-ASP-HGH—methionyl-aspartyl human growth hormone.

ori—the origin of replication.

Permissive Temperature—the temperature range throughout which a temperature-sensitive gene product functions in a manner similar to its wild-type counterpart.

pL—the phage lambda leftward transcriptional activating sequence.

Promoter—a DNA sequence that directs transcription of DNA into RNA.

Recombinant DNA Cloning Vector—any autonomously replicating or integrating agent, including, but not limited to, plasmids, comprising a DNA molecule to which one or more additional DNA molecules can be or have been added.

Recombinant DNA Expression Vector—any autonomously replicating or integrating agent, including, but not limited to, plasmids, comprising a DNA molecule that encodes a transcriptional and translational activating sequence and to which one or more additional DNA molecules encoding functional polypeptides can be or have been added so as to be expressed from the activating sequence.

Replicon—A DNA sequence that controls and allows for autonomous replication of a plamid or other vector.

Restriction Fragment—any linear DNA molecule generated by the action of one or more restriction enzymes.

Selectable Marker—a DNA sequence, such as an antibiotic resistance-conferring gene, that encodes an activity that provides a basis for selection, such that only cells that comprise the DNA sequence can grow and divide.

Restrictive Temperature—the temperature range throughout which a temperature-sensitive gene product does not function or functions ineffectively as compared to the wild-type gene product.

Sensitive Host Cell—a host cell that cannot grow in the presence of a given antibiotic without a DNA segment that confers resistance thereto.

Structural Gene—DNA that encodes the amino acids comprising a functional polypeptide but lacks transcriptional and translational activating sequences.

TcR—the tetracycline-resistant phenotype or gene conferring the same.

Transcriptional Activating Sequence—a DNA sequence that directs transcription of DNA into RNA.

Transformant—a recipient host cell that has undergone transformation.

Transformation—the introduction of DNA into a recipient host cell that changes the genotype and results in a change in the recipient cell.

Translational Activating Sequence—any DNA sequence, including the Shine-Dalgarno sequence and translational start codon, such as 5'-ATG-3', but not including any sequences downstream from the start codon, that provides for the initiation of translation of a mRNA transcript into a peptide or polypeptide.

DETAILED DESCRIPTION OF THE FIGURES

DETAILED DESCRIPTION OF THE INVENTION

Figure 1:
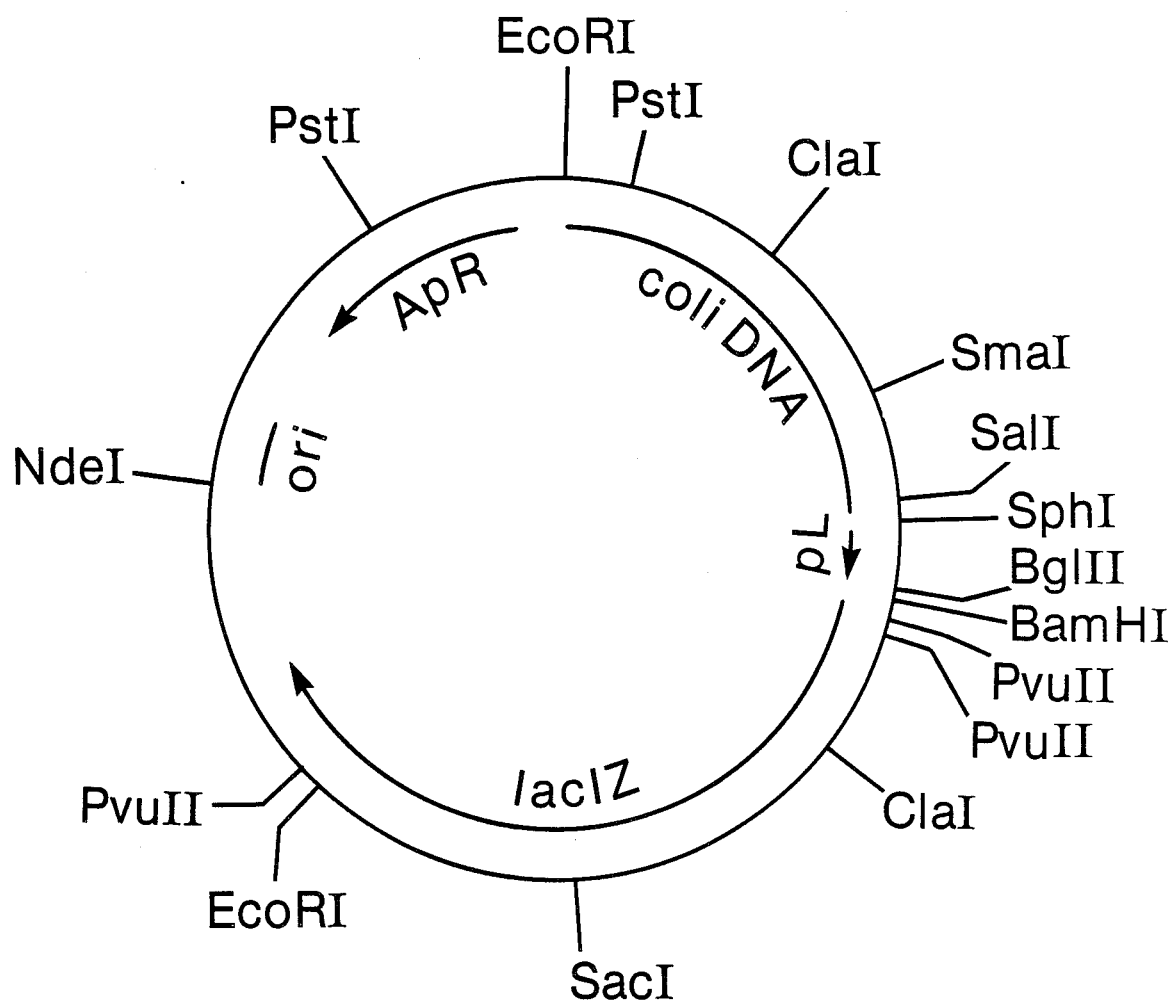
FIG. 1 is a restriction site and funct map of plasmid pKC283.

The present invention concerns a novel, hybrid pL-lpp transcriptional and translational activating sequence, recombinant DNA expression vectors that comprise the novel activating sequence, and host cells transformed with the expression vectors of the present invention. The novel activating sequence of the present invention has the following structure:

```
             10            20            30
5'-GATCTCTCAC CTACCAAACA ATGCCCCCT
   |||||||||| |||||||||| ||||||||||
3'-CTAGAGAGTG GATGGTTTGT TACGGGGGGA 40            50            60
   GCAAAAAATA AATTCATATA AAAAACATAC
   |||||||||| |||||||||| ||||||||||
   CGTTTTTTAT TTAAGTATAT TTTTTGTATG 70            80            90
   AGATAACCAT CTGCGGTGAT AAATTATCTC
   |||||||||| |||||||||| ||||||||||
   TCTATTGGTA GACGCCACTA TTTAATAGAG 100           110           120
   TGGCGGTGTT GACATAAATA CCACTGGCGG
   |||||||||| |||||||||| ||||||||||
   ACCGCCACAA CTGTATTTAT GGTGACCGCC 130           140           150
   TGATACTGAG CACATCAGAT CTATTAACTC
   |||||||||| |||||||||| ||||||||||
   ACTATGACTC GTGTAGTCTA GATAATTGAG 160          170
   AATCTAGAGG GTATTAATAA TG-3'
   |||||||||| |||||||||| ||
   TTAGATCTCC CATAATTATT AC-5'
```

The novel activating sequence of the present invention has many features not readily observable from the nucleotide sequence depicted above. Nucleotides 1-138 of the sequence are derived from the lambda leftward promoter, whereas nucleotides 143-172 are derived from the E. coli lpp translational activating sequence. Nucleotides 139-142 are derived neither from lambda nor from the E. coli lpp gene but instead were generated in the fusion of the pL transcriptional activating sequence to the lpp translational activating sequence. Nucleotides 1-138 encode not only the pL transcriptional activating but also three pL operator sequences, which serve as repressor binding sites. The operator sequences are encoded at residues 65-81, 85-101, and 109-125. Messenger RNA (mRNA) transcription begins at the deoxyadenyl residue at position 134 in wild-type lambda and proceeds toward the translational start codon; presumably, mRNA transcription begins at the same position in the novel activating sequence of the present invention. The translational start codon of the coding sequence to be expressed is located at residues 170-172, which are 5'-ATG-3'.

Two restriction enzyme sites in the activating sequence of the present invention are particularly useful. A BglII site located at residues 137-142 allows for substitution of the lpp translational activating sequence with other activating sequences and also allows for nearly complete control over the sequence of the RNA to be transcribed from the pL promoter. The XbaI site at residues 153-158 provides a convenient site for the insertion of functional polypeptide-encoding DNA, although the inserted DNA must also comprise sequences that reconstruct the activating sequence of the present invention. The XbaI site could also be used in conjunction with the BglII site for translational activating sequence substitutions.

The number of nucleotides between the transcriptional start site, at residue 134, and the translational start site, at residue 170, is also an important feature of the novel activating sequence of the present invention. Most E. coli genes have about 20-40 nucleotides between the transcriptional start site and translational start codon. The transcriptional translational activating sequence of the present invention, with about 36 nucleotides between the transcriptional and translational start sites, is therefore typical of most E. coli activator sequences. In contrast, most of the expression vectors disclosed in the prior art that utilize the lambda pL transcriptional activating sequence comprise well over one hundred nucleotides between the transcriptional start site and the translational start codon.

Preferred expression vectors of the present invention comprise not only the novel activating sequence, but also a replicon that allows extrachromosomal maintenance of the vector, a selectable marker, and a DNA sequence that encodes a functional polypeptide. More preferred expression vectors of the present invention further comprise a gene that encodes a temperature-sensitive repressor of the lambda pL transcriptional activating sequence. The most preferred expression vectors of the present invention comprise the novel activating sequence, a tetracycline resistance-conferring gene, the lambda cI857 gene, and a DNA sequence that encodes a functional polypeptide, such as enterokinase-linked bovine growth hormone (EK-BGH) or methionylaspartylhuman growth hormone (MET-ASP-HGH).

The prototype expression vector of the present invention, into which any gene of interest can be inserted and expressed, was constructed using plasmid pKC283 as starting material. Plasmid pKC283 is ~9 kilobases (kb) in size and can be conventionally isolated from *E. coli* K12 BE1201/pKC283, a strain deposited and made part of the permanent stock culture collection of the Northern Regional Research Laboratory, Peoria, Ill. 61604. The strain is available to the public as a preferred source and stock reservoir of plasmid pKC283 under the accession number NRRL B-15830. *E. coli* K12 BE1201/pKC283 may carry two different plasmids that can be conventionally isolated and separated on the basis of size and the pattern of restriction sites. A restriction site and function map of plasmid pKC283 is provided in FIG. 1 of the accompanying drawings.

Plasmid pKC283 comprises the lambda pL transcriptional activating sequence and a bacteriophage T7 late gene translational activating sequence connected in translational reading phase with a gene encoding β-galactosidase activity. Sequences from a λ$_{lac}$ transducing phage are encoded at the 3' end of the β-galactosidase-encoding DNA. The replicon of plasmid pKC283 is derived from plasmid pBR322, but because the ~2.1 kb EcoRI-PvuII restriction fragment of plasmid pBR322 has been replaced by the lambda pL, bacteriophage T7, and β-galactosidase-encoding sequences in plasmid pKC283, plasmid pKC283 is rop⁻. A plasmid with the rop⁻ mutation, described in Cesaremi et al., 1982, Proc. Natl. Acad. Sci. U.S.A. 79:6313 and Som et al., 1983, Proc. Natl. Acad. Sci. U.S.A. 80:3232, has a copy number in *E. coli* about 5X higher than plasmid pBR322.

All of the expression vectors of the present invention exemplified herein utilize the rop⁻ derivative of the plasmid pBR322 replicon. However, the high level of expression of functional polypeptide achieved by host cells transformed with the plasmids of the present invention is due, primarily, to the novel transcriptional and translational activating sequence disclosed herein. Consequently, the present invention also comprises the use of the novel activating sequence to drive expression of functional polypeptides from expression vectors that utilize other plasmid replicons, such as the runaway replicon described in U.S. Pat. No. 4,487,835, or phage (viral) sequences for the purpose of introducing and/or maintaining the expression vector in the host cell.

Figure 2:
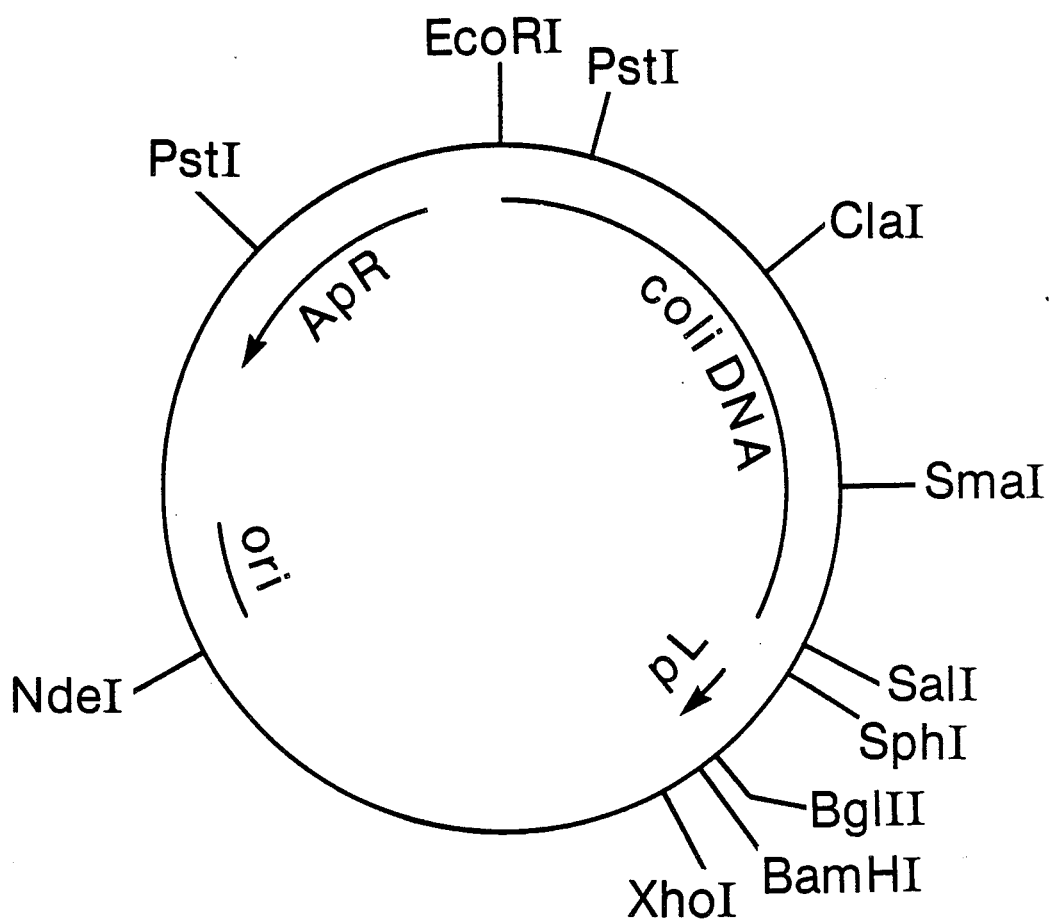
FIG. 2 is a restriction site and function map of plasmid pKC283PX.

In order to construct the expression vector of the present invention, plasmid pKC283 was digested with PvuII, ligated to XhoI linkers, and recircularized to form plasmid pKC283PX. These steps deleted ~3.0 kb of the β-galactosidase-encoding DNA and placed an XhoI restriction enzyme recognition site where the deletion took place. A restriction site and function map of plasmid pKC283PX is presented in FIG. 2 of the accompanying drawings.

Figure 3:
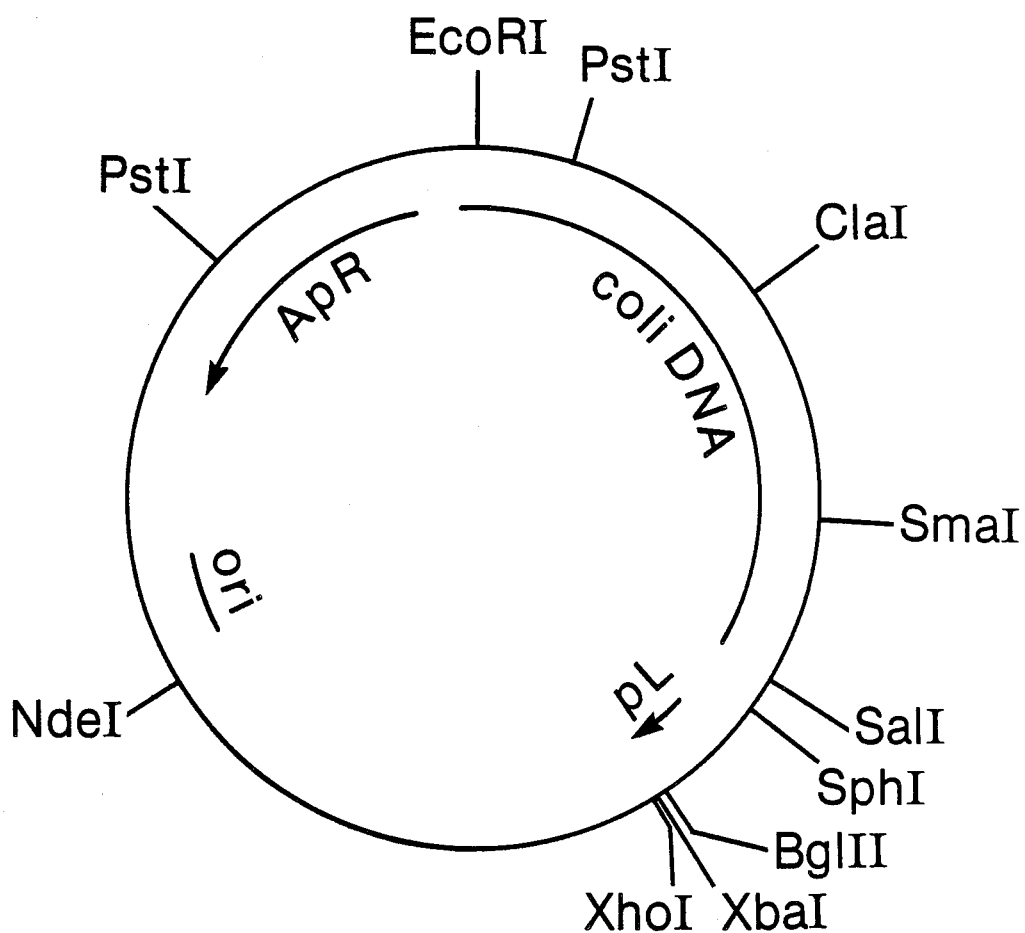
FIG. 3 is a restriction site and function map of plasmid pKC283-L.

Plasmid pKC283PX was digested with restriction enzymes BglII and XhoI, and a synthetic linker encoding an XbaI restriction enzyme recognition sequence and part of the *E. coli* lpp translational activating sequence site was introduced into the BglII-XhoI-digested plasmid pKC283PX. Essentially, this latter step merely replaced ~0.15 kb of β-galactosidase encoding DNA with a synthetic DNA fragment. The resulting plasmid was designated pKC283-L; a restriction site and function map of plasmid pKC283-L is presented in FIG. 3 of the accompanying drawings.

Figure 4:
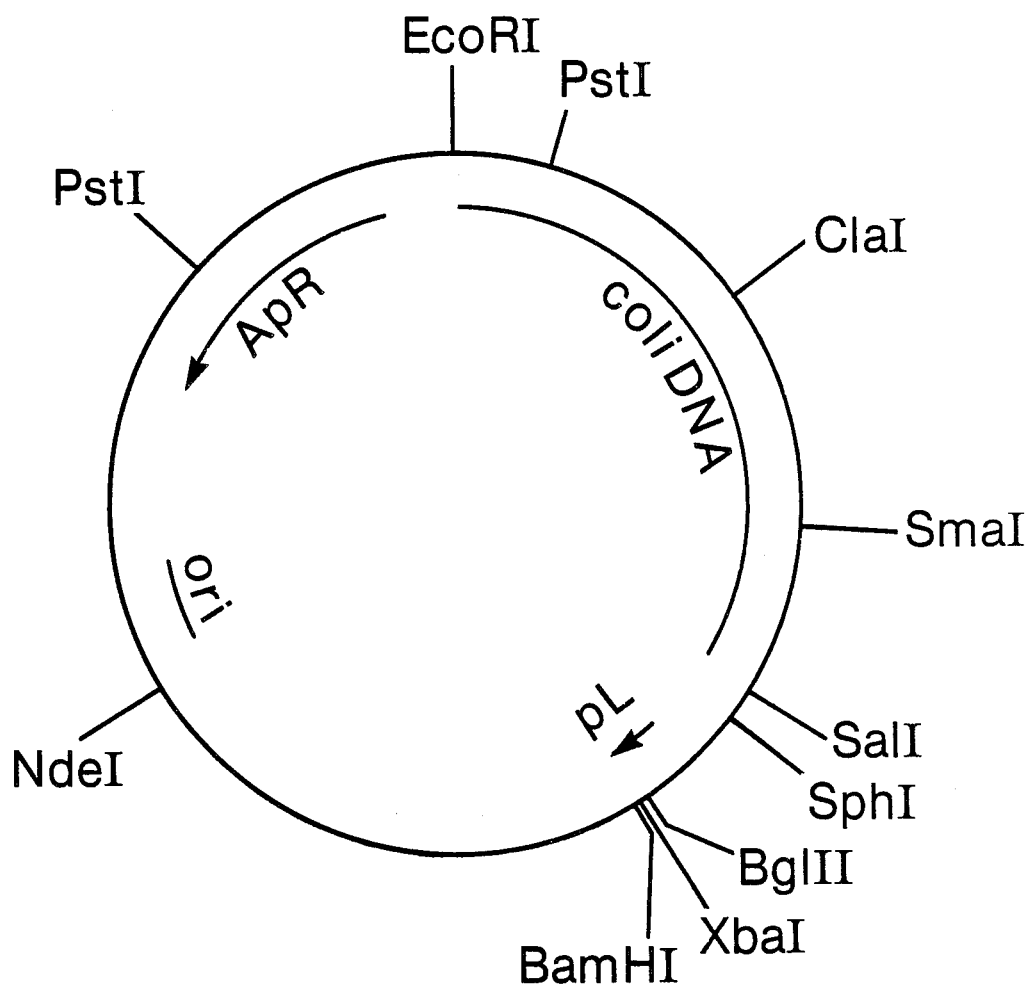
FIG. 4 is a restriction site and function map of plasmid pKC283-LB.

Plasmid pKC283-L was digested with XhoI, treated with DNA polymerase I large fragment (Klenow), ligated to BamHI linkers, digested with BamHI, and religated to form plasmid pKC283-LB. -Plasmid pKC283-LB does not comprise the entire activating sequence of the present invention but can still be used to construct expression-on vectors. The XbaI and BamHI sites on plasmid pKC283-LB are situated so that functional polypeptide-encoding DNA can be introduced into plasmid pKC283-LB as an XbaI-BamHI restriction fragment. High-level expression of the functional polypeptide-encoding DNA will occur when the XbaI-BamHI restriction fragment comprises sequences that reconstruct the novel activating sequence of the present invention. A restriction site and function map of plasmid pKC283-LB is presented in FIG. 4 of the accompanying drawings.

Figure 5:
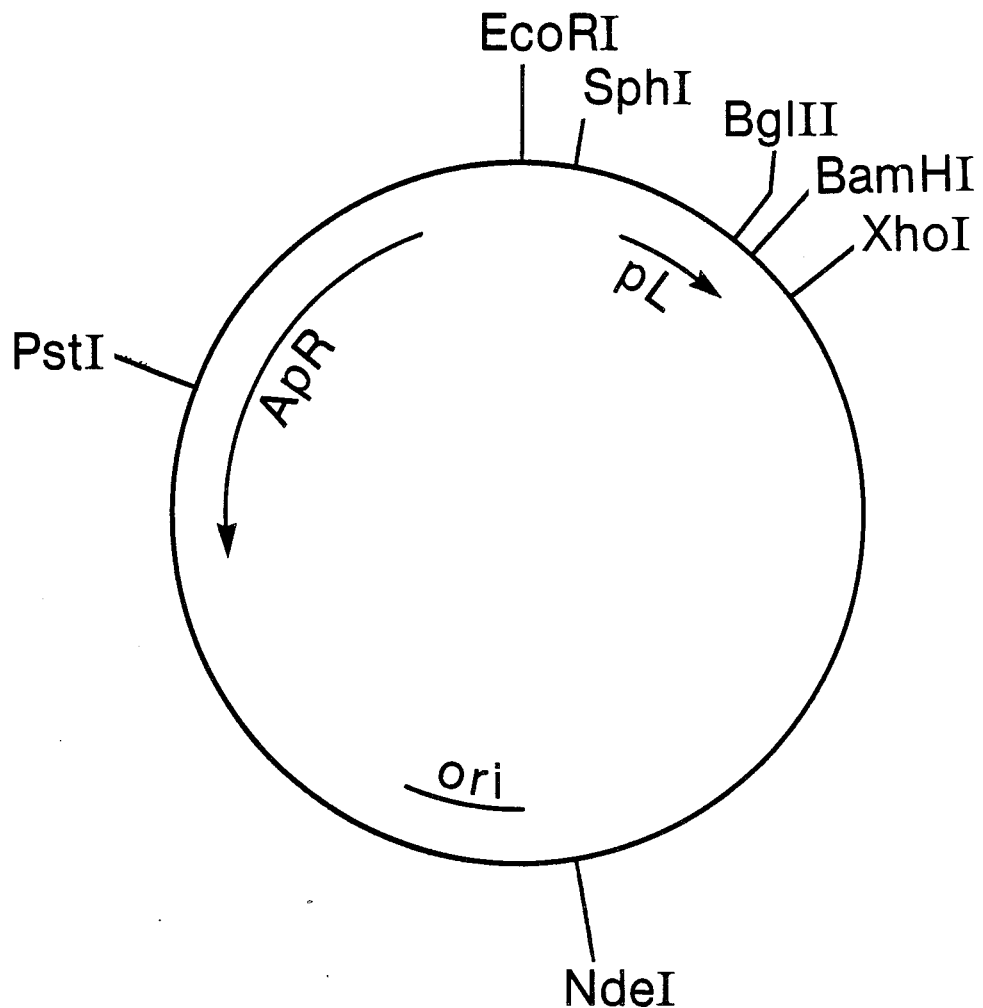
FIG. 5 is a restriction site and function map of plasmid pKC283PRS.
Figure 6:
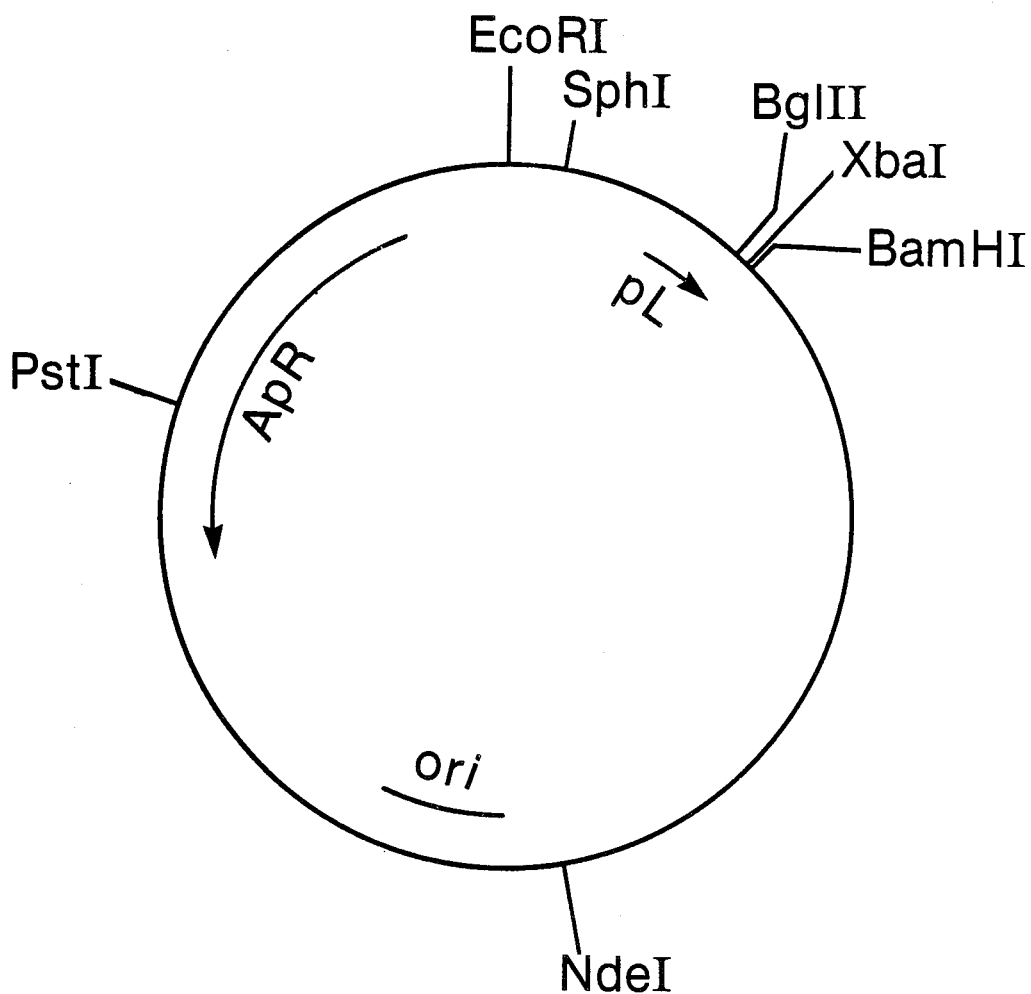
FIG. 6 is a restriction site and function map of plasmid pL32.

Plasmid pKC283-LB comprises ~2.1 kb of *E. coli* DNA that is unnecessary for expression vector functions. In order to reduce the size of plasmid pKC283-LB, the following replacement reaction was carried out. Plasmid pKC283PX was digested with SalI, treated with Klenow, ligated to EcoRI linkers, digested with EcoRI, and recircularized by ligation to yield plasmid pKC283PRS. A restriction site and function map of plasmid pKC283PRS is presented in FIG. 5 of the accompanying drawings. Plasmid pKC283PRS was then digested with restriction enzymes PstI and SphI, and the resulting ~0.85 kb restriction fragment was isolated from the other digestion products and purified. Plasmid pKC283-LB was digested with PstI and SphI, and the resulting ~3.0 kb restriction fragment was isolated and purified. The purified fragments were then ligated together to form plasmid pL32. A restriction site and function map of plasmid pL32 is presented in FIG. 6 of the accompanying drawings.

Figure 7:
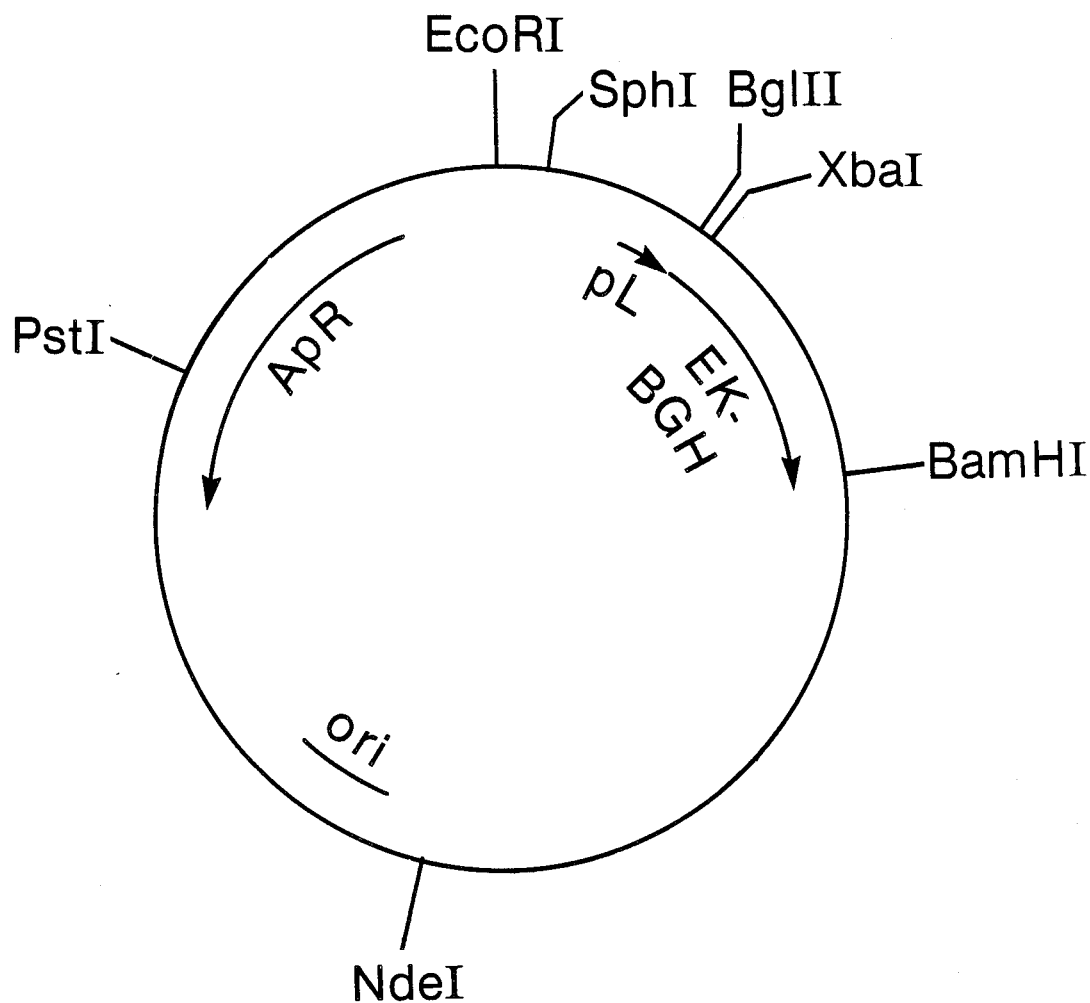
FIG. 7 is a restriction site and function map of plasmid pL47.
Figure 14:
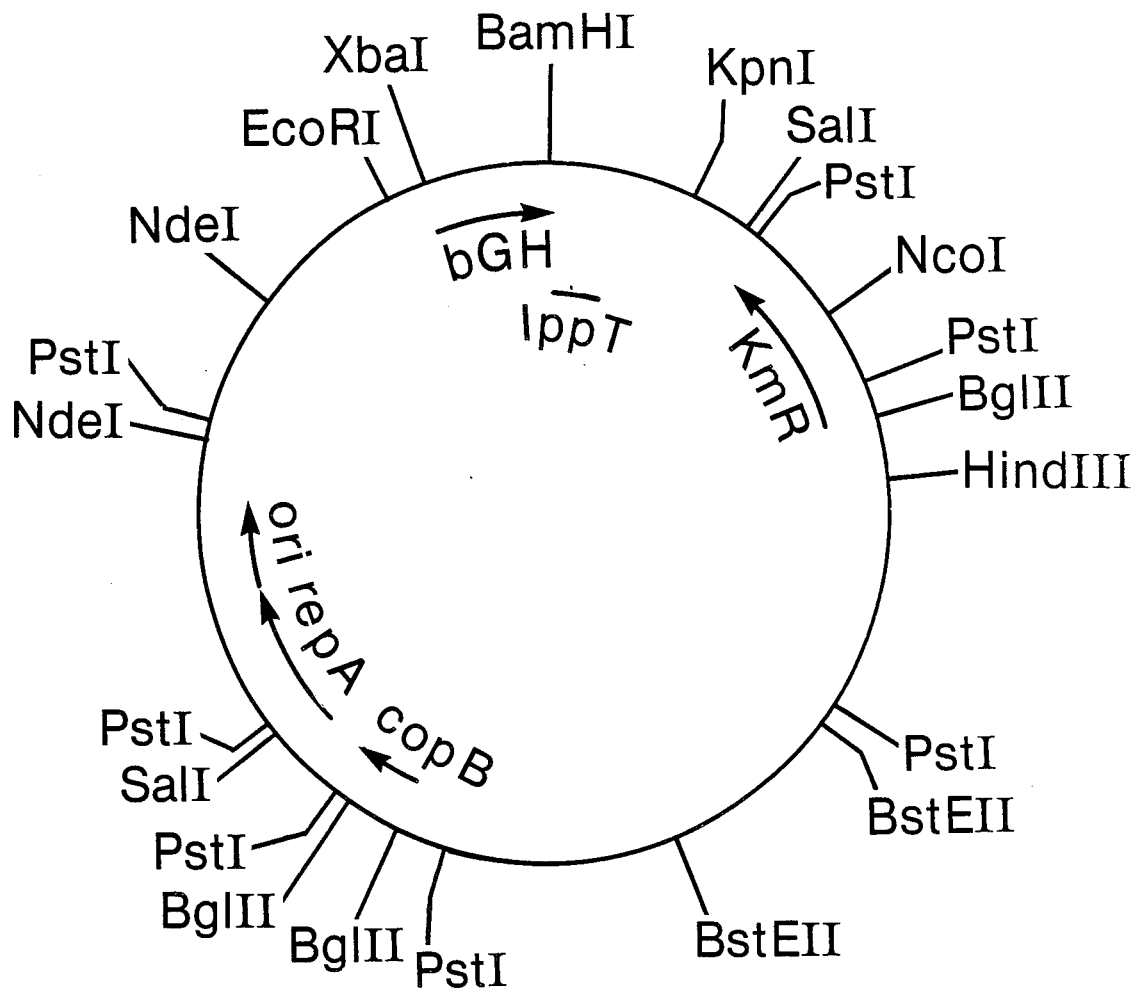
FIG. 14 is a restriction site and function map of plasmid pCC101.

Although an intermediate plasmid in the construction of the expression vector of the present invention, plasmid pL32 can drive expression of an inserted functional polypeptide-encoding DNA fragment. A derivative of plasmid pL32, designated pL47, was constructed by insertion of an XbaI-BamHI restriction fragment encoding Met-Phe-Pro-Leu-Asp-Asp-Asp-Asp-Lys-bovine growth hormone (EK-bGH). The Xba-BamHI restriction fragment also comprised sequences that, when inserted into plasmid pKC283-LB, reconstructed the novel activating sequence of the present invention. The XbaI-BamHI restriction fragment is ~0.6 kb and originates from plasmid pCC101. The construction of plasmid pCC101 is disclosed in Example 3 of U.S. Pat. No. 4,745,069, incorporated herein by reference. A restriction site and function map of plasmid pCC101 is presented in FIG. 14 of the accompanying drawings. A restriction site and function map of plasmid pL47 is presented in FIG. 7 of the accompanying drawings.

Plasmid pL47 is lethal to *E. coli* host cells which do not possess a lambda pL repressor gene. Initiation of transcription from the lambda pL promoter is known to be repressed to levels below detection limits by the product of the lambda gene cI. Mutants of the cI gene are available that code for a temperature-sensitive repressor (Lieb, M., 1966, J. Mol. Biol. 16:149), so that transcription from pL is repressed at low temperature and is initiated at high temperature. Because of the availability of repressor genes such as cI, the lambda pL promoter has the distinct advantage of being controllable in *E. coli*, a characteristic which is desirable where large-scale microbial fermentation production is concerned. The lambda cro gene product also represses transcription from the pL promoter.

As stated above, uncontrolled transcription from the lambda pL promoter of the EK-BGH-encoding DNA is lethal to *E. coli* transformed with plasmid pL47. In the presence of repressor, however, the lambda pL promoter does not function, and no EK-BGH is expressed by *E. coli*/pL47 transformants. To obtain good production of EK-BGH, the *E. coli*/pL47 transformants must comprise a gene that encodes a temperature-sensitive repressor of the lambda pL promoter, so that lambda pL can be repressed while the cells are being cultured to the appropriate cell density for expression. The cI857 gene encodes a temperature-sensitive repressor of the lambda pL promoter. *E. coli*/pL47 transformants that comprise the cI857 gene, either on an extrachromosomally-replicating vector or integrated into the chromosome, can be cultured at the permissive temperature and EK-BGH expressed at levels approaching 30% of the total cellular protein at the restrictive temperature.

Figure 8:
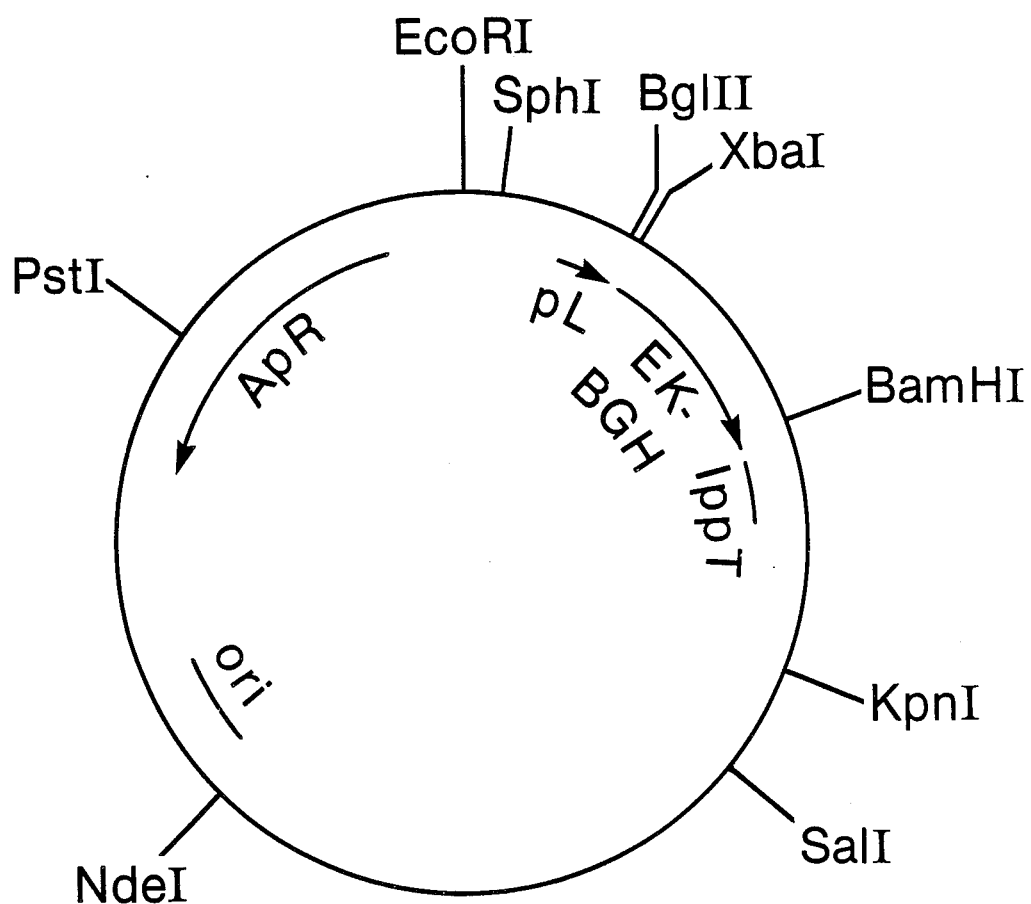
FIG. 8 is a restriction site and function map of plasmid pL84.

The presence of a transcription terminator at the 3' end of the expressed gene of expression vectors such as pL47 is known to enhance expression. Because the sequence downstream of the 3' end of the EK-BGH-encoding DNA on plasmid pL47 originated from the λ$_{lac}$ transducing phage and was not known to encode a transcription terminator, a vector was constructed to replace the sequences at the 3' end of the EK-BGH-encoding DNA of plasmid pL47 with sequences known to encode the *E. coli* lpp terminator. The *E. coli* lpp terminator can be easily isolated from plasmid pCC101. In order to construct the desired plasmid with the lpp terminator at the 3' end of the EK-BGH-encoding DNA, plasmid pL32 was digested with BamHI, treated with Klenow, ligated to SalI linkers, digested with SalI, and then digested with XbaI. The resulting ~3.9 kb DNA fragment had SalI and XbaI cohesive ends and was then ligated to the ~1.62 kb XbaI-SalI restriction fragment of plasmid pCC101. This latter ~1.62 kb restriction fragment encodes EK-BGH and the lpp transcription terminator in the desired orientation. The plasmid resulting from the ligation of the XbaI-SalI restriction fragments described above was designated plasmid pL84. A restriction site and function map of plasmid pL84 is presented in FIG. 8 of the accompanying drawings.

Figure 9:
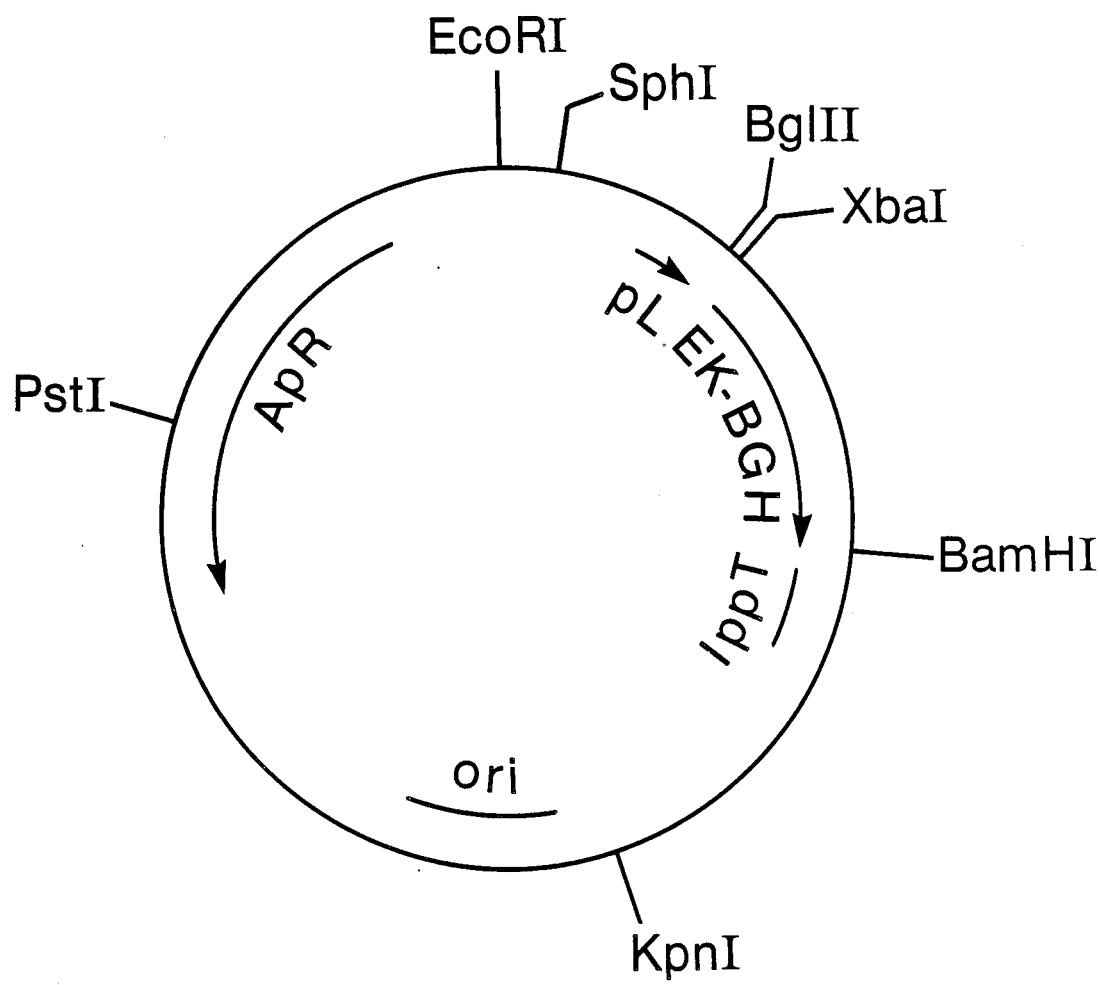
FIG. 9 is a restriction site and function map of plasmid pL95.

To delete extraneous DNA at the 3' end of the lpp terminator, plasmid pL84 was digested with NdeI, treated with Klenow, ligated to KpnI linkers, digested with KpnI, and recircularized by ligation to yield plasmid pL95. A restriction site and function map of plasmid pL95 is presented in FIG. 9 of the accompanying drawings. When *E. coli*/pL95 transformants comprising the temperature-sensitive cI857 gene product are cultured for expression of EK-BGH, the desired EK-BGH accumulates to levels approaching 30% of total cellular protein. Therefore, despite the presence of a defined terminator on plasmid pL95, plasmids pL47 and pL95 drive expression of EK-BGH to about the same extent.

Because plasmids pL47 and pL95 drive expression of EK-BGH equally well, and because plasmid pL47 comprises λ$_{lac}$ transducing phage sequences at the 3' end of the EK-BGH-encoding sequences, the λ$_{lac}$ transducing phage sequences on plasmid pL47 probably encode a transcription terminator.

However, neither plasmid pL47, nor plasmid pL95, are ideal expression vectors. Both plasmids utilize an ampicillin resistance-conferring gene for selection purposes. Because the ampicillin resistance-conferring enzyme destroys the ampicillin in the media, high levels of the antibiotic need to be maintained in the fermentation broth in order that the ampicillin not be depleted. Of course, depletion of the ampicillin would allow cells that do not comprise an expression plasmid to flourish, resulting in low yields of the desired product. The use of a tetracycline resistance-conferring gene as a selectable marker eliminates the need for high levels of antibiotic and the problem of plasmid loss. The tetracycline resistance-conferring mechanism affects the permeability of the host cell membrane and does not inactivate the tetracycline in the media. Therefore, plasmids pL47 and pL95 could be improved by replacing the ampicillin resistance-conferring gene on the plasmids with the tetracycline resistance-conferring gene.

Plasmids pL47 and pL95 could also be improved by placing the cI857 gene on the same plasmid as the pL promoter. As described above, *E. coli* transformants of plasmid pL47 or plasmid pL95 require the presence of the cI857 gene product, with the cI857 gene encoded either in the chromosome of the host cell or in a separate extrachromosomal vector, to prevent the plasmids from being lethal to the host cell during the period of culture to obtain the requisite number of cells for expression. However, the presence of the cI857 gene in either the host cell chromosomal DNA or a separate vector can result in there being more copies of the pL-lpp hybrid transcriptional and translational activating sequence of the present invention in the host cell than copies of the cI857 gene or gene product. Such a deficiency of cI857 gene product would result in expression of the gene driven by the pL-lpp hybrid transcriptional and translational activating sequence. Because many recombinant gene products exert deleterious effects on the host cell, regulated expression such that a gene product is expressed only when the culture at a certain density and condition is highly desirable. Such regulated expression can be assured by placing the cI857 gene on the same expression vector as the pL-lpp hybrid transcriptional and translational activating sequence of the present invention.

Figure 10:
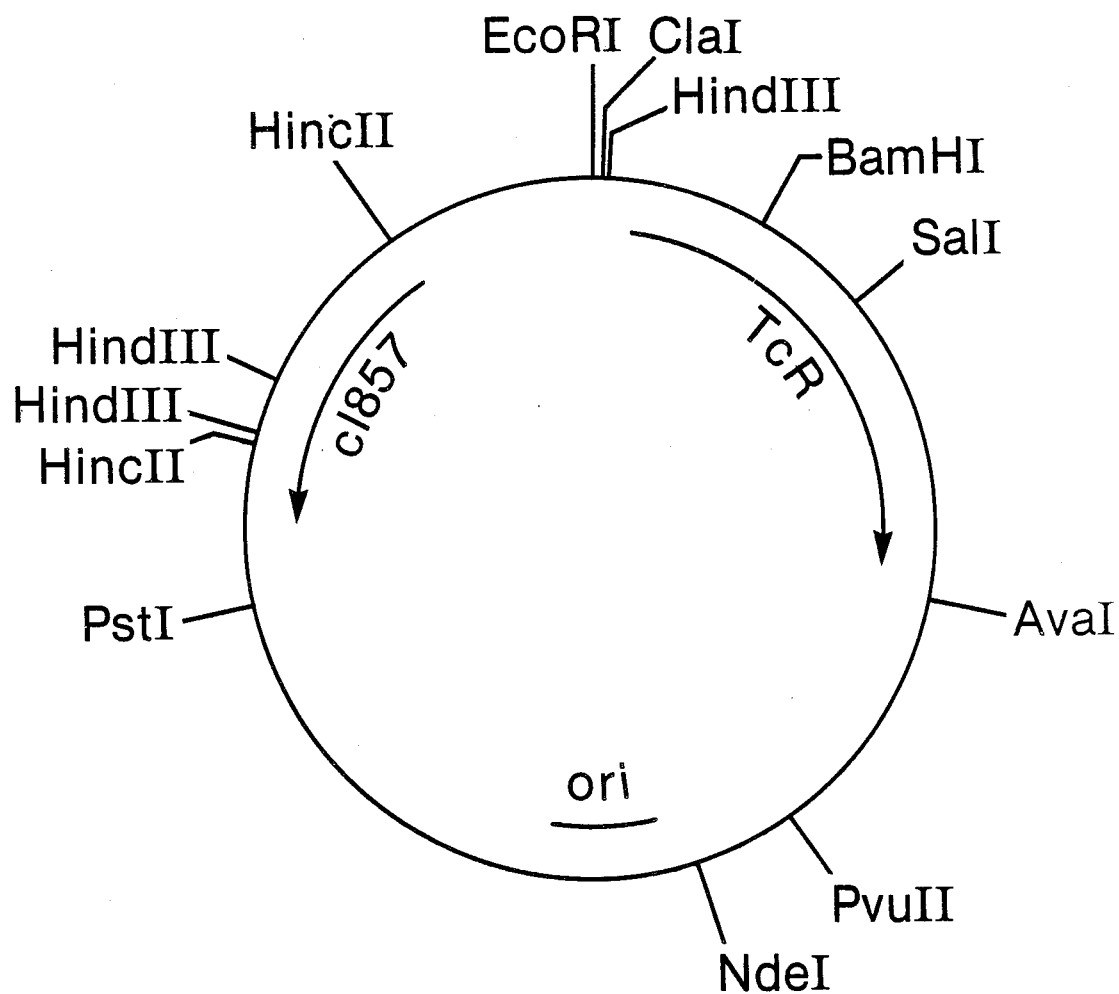
FIG. 10 is a restriction site and function map of plasmid pPR12.
Figure 11:
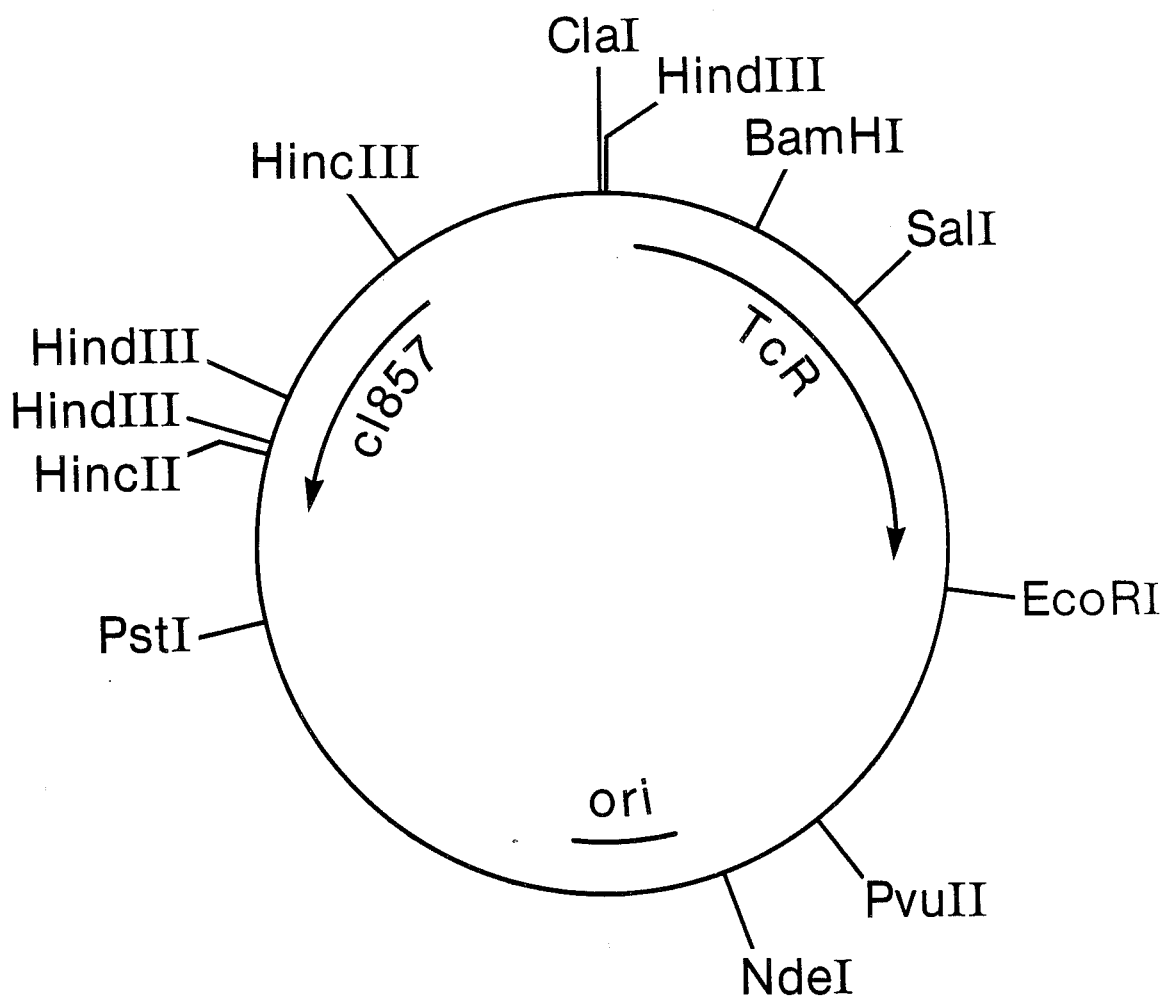
FIG. 11 is a restriction site and function map of plasmid pPR12AR1.

The improvements of pL47 and pL95 discussed above were achieved in the following manner. The desired cI857 and tetracycline resistance-conferring genes were isolated from plasmid pPR12, which is disclosed and claimed in U.S. Pat. No. 4,436,815, issued Mar. 13, 1984. A restriction site and function map of plasmid pPR12 is presented in FIG. 10 of the accompanying drawings. To isolate both the cI857 and tetracycline resistance-conferring genes on a PstI-EcoRI restriction fragment, plasmid pPR12 was digested with EcoRI, treated with Klenow, and recircularized by ligation to yield plasmid pPR12ΔR1. Plasmid pPR12ΔR1 was digested with AvaI, treated with Klenow, ligated to EcoRI linkers, digested with EcoRI, and recircularized by ligation to yield plasmid pPR12AR1. A restriction site and function map of plasmid pPR12AR1 is presented in FIG. 11 of the accompanying drawings.

Figure 12:
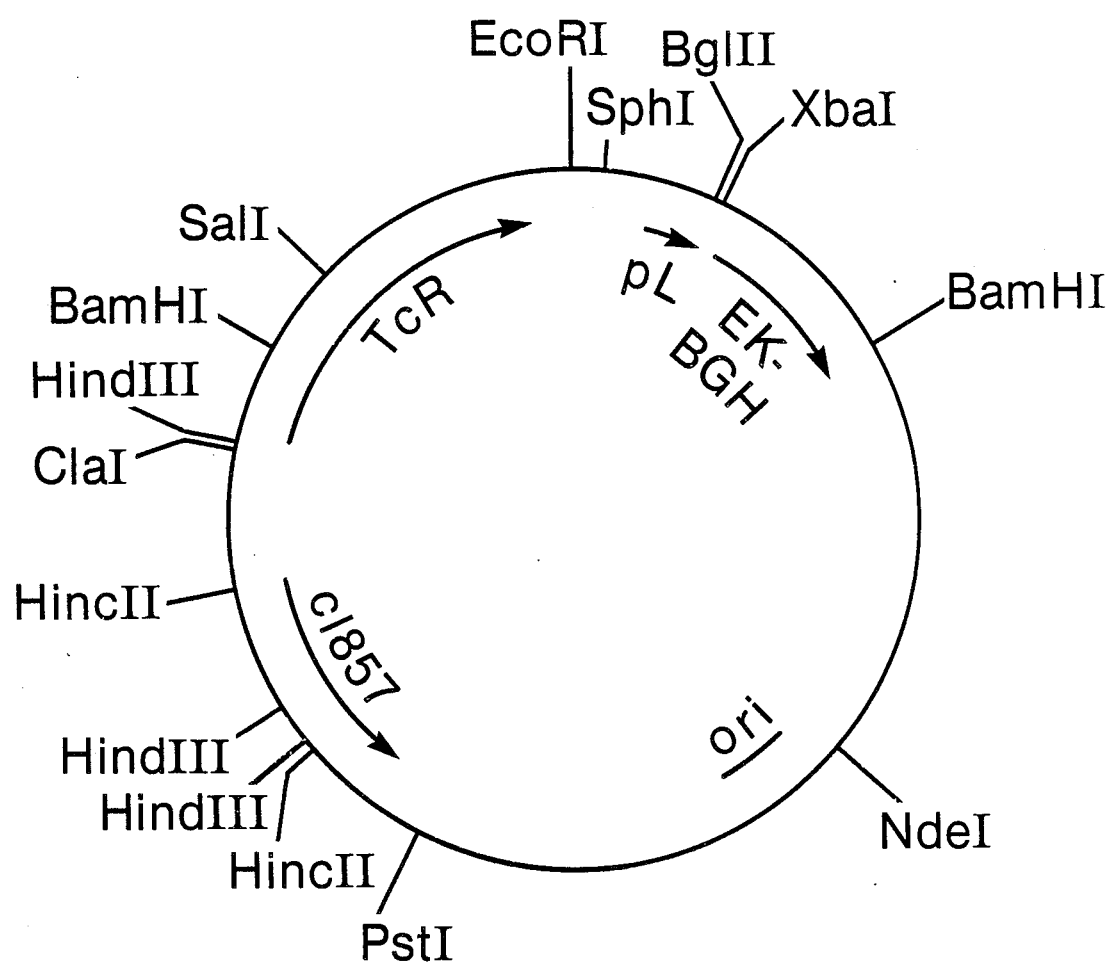
FIG. 12 is a restriction site and function map of plasmid pL110.
Figure 13:
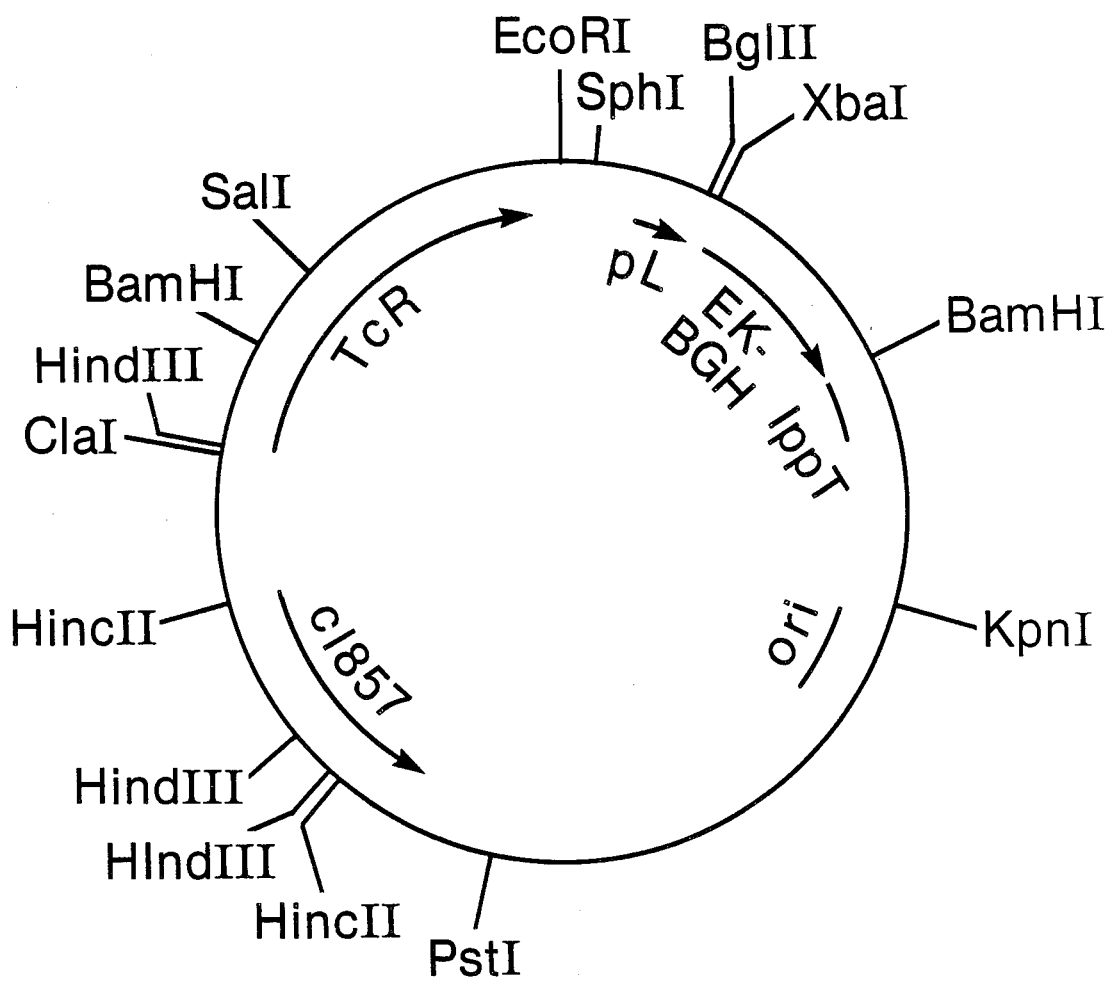
FIG. 13 is a restriction site and function map of plasmid pL111.

The ~2.9 kb PstI-EcoRI restriction fragment of plasmid pPR12AR1 was ligated to the ~1.03 kb EcoRI-BamHI and ~2.7 kb BamHI-PstI restriction fragments of plasmid pL47 to yield plasmid pL110. A restriction site and function map of plasmid pL110 is presented in FIG. 12 of the accompanying drawings. In an analogous construction, the ~2.9 kb PstI-EcoRI restriction fragment plasmid pPR12AR1 was ligated to the ~1.03 kb EcoRI-BamHI restriction fragment of plasmid pL47 and to the ~2.03 kb BamHI-PstI restriction fragment of plasmid pL95 to yield plasmid pL111. A restriction site and function map of plasmid pL111 is presented in FIG. 13 of the accompanying drawings.

Plasmids pL110 and pL111 are useful, controllable expression vectors. A variety of functional polypeptide-encoding DNA fragments can be introduced into and expressed from plasmids pL110 and pL111. The functional polypeptide-encoding DNA is best introduced into the plasmid on an XbaI-BamHI restriction fragment, in a reaction that replaces the EK-BGH-encoding DNA of plasmids pL110 and pL111 with the functional polypeptide-encoding DNA desired to be expressed. The modifications necessary to convert any functional polypeptide-encoding DNA into the required XbaI-BamHI restriction fragment employ reactions within the capacity of one skilled in the art.

Plasmid pL110 serves as starting material in the construction of plasmid pNM1093, a plasmid that utilizes the activating sequence of the present invention to drive expression of MET-ASP-HGH in *E. coli* host cells. Plasmid pNM1093 is constructed by ligating the ~6.0 kb XbaI-BamHI restriction fragment of plasmid pL110 to an ~0.6 kb XbaI-BamHI restriction fragment that encodes a small portion of the transcriptional and translational activating sequence of the present invention and the complete coding sequence MET-SP-HGH. Plasmid pNM1093 is ~6.6 kb in size; *E. coli* K12 RV308/pNM1093 transformants express MET-ASP-HGH at levels approaching 30% of the total cellular protein when cultured at the restrictive temperature for the cI857 gene product.

The following Examples describe the construction of the expression vectors of the present invention.

EXAMPLE 1

Isolation of Plasmid pKC283

Lyophils of *E. coli* K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 μg/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 μg/ml ampicillin in a manner so as to obtain a single colony isolate of *E. coli* K12 BE1201/pKC283. The single colony obtained was inoculated into 10 ml of LB medium containing 50 μg/ml ampicillin and incubated overnight at 32° C. with vigorous shaking. The 10 ml overnight culture was inoculated into 500 ml LB medium and incubated at 32° C. with vigorous shaking until the culture reached stationary phase.

The following procedure is adapted from Maniatis et al., 1982, Molecular Cloning (Cold Spring Harbor Laboratory).

The cells were harvested by centrifugation at 4000 g for 10 minutes at 4° C., and the supernatant was discarded. The cell pellet was washed in 100 ml of ice-cold STE buffer (0.1 M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2 N NaOH and 1% SDS) were then added to the lysozyme-treated cells, and the solution was gently mixed by inversion. The mixture was incubated on ice for 10 minutes.

Fifteen ml of ice-cold 5 M potassium acetate, pH 4.8, were added to the lysed-cell mixture and the solution mixed by inversion. The solution was incubated on ice for 10 minutes. The 5 M potassium acetate solution was prepared by adding 11.5 ml of glacial acetic acid to 28.5 ml of water and 60 ml of 5 M potassium acetate; the resulting solution is 3M with respect to potassium and 5 M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentration was about 600 μg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 μg/ul. A restriction site and function map of plasmid pKC283 is presented in FIG. 1 of the accompanying drawings.

EXAMPLE 2

Construction of Plasmid pKC283PX

About 10 μl of the plasmid pKC283 DNA prepared in Example 1 were mixed with 20 μl 10 X medium-salt restriction buffer (500 mM NaCl; 100 mM Tris-HCl, pH 7.5; 100 mM MgCl$_2$; and 10 mM DTT), 20 μl 1 mg/ml BSA, 5 μl restriction enzyme PvuII (~50 Units, as defined by Bethesda Research Laboratories (BRL), from which all restriction enzymes used herein were obtained), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 μl of TE buffer.

About 600 picomoles (pM) of XhoI linkers (5'-CCTCGAGG-3') were kinased in a mixture containing 10 μl 5 X Kinase Buffer (300 mM Tris-HCl, pH 7.8; 50 mM MgCl$_2$; and 25 mM DTT), 5 μl 5 mM ATP, 24 μl H$_2$O, 0.5 μl of T4 polynucleotide kinase (about 2.5 units as defined by P-L Biochemicals), 5 μl 1 mg/ml BSA, and 5 μl of 10 mM spermidine by incubating the mixture at 37° C. for 30 minutes.

About 12.5 μl of the kinased XhoI linkers were added to the 5 μl of PvuII-digested plasmid pKC283 DNA, and then 2.5 μl of 10 X ligase buffer (300 mM Tris-HCl, pH 7.6; 100 mM MgCl$_2$; and 50 mM DTT, 2.5 μl of 1 mg/ml BSA, 7 μl of 5 mM ATP, 2.5 μl (about 2.5 units as defined by P-L Biochemicals) of T4 DNA ligase, 2.5 μl of 10 mM spermidine, and 3 μl of water were added to the DNA. The resulting ligation reaction was incubated at 4° C. overnight. After the ligation reaction, the reaction mixture was adjusted to have the composition of high-salt buffer (0.1 M NaCl; 0.05 M Tris-HCl, pH 7.5; 10.0 mM MgCl$_2$; and 1 mM DTT). About 10 μl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 2 of the accompanying drawings.

EXAMPLE 3

Construction of E. coli K12 MO(λ+)/pKC283PX

E. coli K12 MO(λ+) can be obtained from the Northern Regional Research Laboratories in lyophylized form under the accession number NRRL B-15993. E. coli K12 MO(λ+) comprises the wild-type lambda pL cI repressor gene, so that transcription from the hybrid pL-lpp promoter of the present invention does not occur in E. coli K12 MO(λ−) cells. The lyophils are reconstituted, single colonies of MO(λ+) are isolated, and a 10 ml overnight culture of the MO(λ+) cells is prepared in substantial accordance with the procedure of Example 1, except that the temperature of incubation is 37° C. and no ampicillin is used in the growth media.

Fifty μl of the overnight culture were used to inoculate 5 ml of LB media which also contained 10 mM MgSO$_4$ and 10 mM MgCl$_2$. The culture was incubated at 37° C. overnight with vigorous shaking. The following morning, the culture was diluted to 200 ml with LB media containing 10 mM MgSO$_4$ and 10 mM MgCl$_2$. The diluted culture was incubated at 37° C. with vigorous shaking until the absorbance at 550 nm ($A_{550}$) was about 0.5, which indicated a cell density of about $1\times10^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM NaCl and then immediately re-pelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared in Example 2; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of LB media in a 125 ml flask and incubated at 37° C. for one hour. One hundred μl aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 1, but the CsCl gradient step was omitted until the desired E. coli K12 MO(λ+)/pKC283PX transformants were identified. A restriction site and function map of plasmid pKC283PX is presented in FIG. 2 of the accompanying drawings

EXAMPLE 4

Construction of E. coli K12 MO(λ+)/pKC283-L

Ten μg of plasmid pKC283PX DNA prepared in accordance with the procedure of Example 1 were dissolved in 20 μl of 10X high-salt buffer, 20 μl 1 mg/ml BSA 5 μl (~50 units) restriction enzyme BglII, 5 μl (~50 units) restriction enzyme XhoI, and 150 μl of water, and the resulting reaction was incubated at 37° C. for two hours. The reaction was stopped, and after precipitating the BglII-XhoI digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 2. The DNA linker had the following structure:

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, Science 198:1056 and in Crea et al., 1978, Proc. Nat. Acad. Sci. USA 75:5765. In addition, an especially preferred method of synthesizing DNA is disclosed in Hsiung et al., 1983, Nucleic Acid Research 11:3227 and Narang et al., 1980, Methods in Enzymology 68:90.

The linker and BglII-XhoI-digested plasmid pKC283PX were ligated in substantial accordance with the procedure of Example 2. The ligated DNA constituted the desired plasmid pKC283-L. A restriction site and function map of plasmid pKC283-L is presented in FIG. 3 of the accompanying drawings. The plasmid pKC283-L DNA was used to transform $E.\ coli$ K12 MO($\lambda^+$) and the resulting $E.\ coli$ K12 MO($\lambda^+$)/pKC283-L transformants were identified in substantial accordance with the procedure of Example 3.

Example 5

Construction of $E.\ coli$ K12 MO($\lambda^+$)/pKC283-LB

About 10 μg of plasmid pKC283-L DNA, prepared in substantial accordance with the procedures of Example 1, were dissolved in 20 μl 10X high-salt buffer, 20 μl 1 mg/ml BSA, 5 μl (~50 units) restriction enzyme XhoI and 155 μl of H$_2$O, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubation in a dry ice-ethanol bath for five minutes, and centrifugation. The resulting DNA pellet was washed with 70% ethanol, dried, and resuspended in 2 μl 10X nick-translation buffer (0.5M Tris-HCl, pH 7.2; 0.1 M MgSO$_4$; and 1 mM DTT), 1 μl of a solution 2 mM in each of the deoxynucleotide triphosphates, 15 μl of H$_2$O, 1 μl (~6 units as defined by P-L Biochemicals) of Klenow, which is the large fragment of $E.\ coli$ DNA polymerase I, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the procedure of Example 2. After the ligation reaction, the DNA was digested with about 100 units of BamHI for about 2 hours at 37° C. in high-salt buffer. After the BamHI digestion, the DNA was prepared for ligation in substantial accordance with the procedure of Example 2.

The ~5.9 kb BamHI restriction fragment was circularized by ligation and transformed into $E.\ coli$ K12 MO($\lambda^+$) in substantial accordance with the procedures of Examples 2 and 3. The $E.\ coli$ K12 MO($\lambda^+$)/pKC283-LB transformants were identified, and then plasmid pKC283-LB DNA was prepared in substantial accordance with the procedure of Example 1. A restriction site and function map of plasmid pKC283-LB is presented in FIG. 4 of the accompanying drawings.

EXAMPLE 6

Construction of $E.\ coli$ K12 MO($\lambda^+$)/pL32

About 10 μg of plasmid pKC283PX were digested with restriction enzyme SalI in high-salt buffer, treated with Klenow, and ligated to EcoRI linkers (5'-GAG-GAATTCCTC-3') in substantial accordance with the procedure of Example 5, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform $E.\ coli$ K12 MO($\lambda^+$) in substantial accordance with the procedure of Example 3. After the $E.\ coli$ K12 MO($\lambda^+$)/pKC283PRS transformants were identified, plasmid pKC283PRS DNA was prepared in substantial accordance with the procedure of Example 1. A restriction site and function map of plasmid pKC283PRS is presented in FIG. 5 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2-3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 μg of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 2. The ligated DNA constituted the desired plasmid pL32. A restriction site and function map of plasmid pL32 is presented in FIG. 6 of the accompanying drawings. Plasmid pL32 was transformed into $E.\ coli$ K12 MO($\lambda^+$) cells in substantial accordance with the procedure of Example 3. Plasmid pL32 DNA was prepared from the $E.\ coli$ K12 MO($\lambda^+$)/pL32 transformants in substantial accordance with the procedure of Example 1. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together.

EXAMPLE 7

Construction of *E. coli* K12 MO(λ+)/pL47

Plasmid pCC101 is disclosed in Example 3 of U.S. Pat. No. 4,745,069, incorporated herein by reference. A restriction site and function map of plasmid pCC101 is presented in FIG. 14 of the accompanying drawings. To isolate the EK-BGH-encoding DNA, about 10 µg of plasmid pCC101 were digested in 200 µl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated and prepared for ligation in substantial accordance with the procedure of Example 6.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid pCC101 in substantial accordance with the procedure of Example 2 to yield plasmid pL47. A restriction site and function map of plasmid pL47 is presented in FIG. 7 of the accompanying drawings. Plasmid pL47 was transformed into *E. coli* K12 MO(λ+) in substantial accordance with the procedure of Example 3, and the *E. coli* K12 MO(λ+)/pL47 transformants were identified. Plasmid pL47 DNA was prepared from the transformants in substantial accordance with the procedures of Example 1.

EXAMPLE 8

Construction of *E. coli* K12 MO(λ+)/pL84

About 10 µg of plasmid pL32 were digested with about 50 units of restriction enzyme BamHI in 200 µl of high-salt buffer at 37° C. for about two hours. The BamHI-digested plasmid pL32 DNA was precipitated, treated with Klenow, and ligated to SalI linkers (5'-CGTCGACG-3') in substantial accordance with the procedure of Example 5. After the SalI linkers were ligated, about 100 units of restriction enzyme SalI and 50 units of restriction enzyme XbaI were added to the ligation mixture, which was adjusted to have the composition of high-salt buffer, and the resulting reaction was incubated at 37° C. for two hours. The reaction products were separated by agarose gel electrophresis, and the ~3.9 kb SalI-XbaI restriction fragment was isolated and prepared for ligation in substantial accordance with the procedure of Example 6.

About 10 µg of plasmid pCC101 were digested with about 50 units each of restriction enzymes SalI and XbaI in 200 ~1 of high-salt buffer at 37° C. for 2 hours. The reaction products were separated by agarose gel electrophoresis, and the ~1.6 kb SalI-XbaI restriction fragment which encodes EK-BGH and the transcription terminator of the *E. coli lpp* gene was isolated and prepared for ligation in substantial accordance with the procedure of Example 6.

The ~3.9 kb SalI-XbaI restriction fragment derived from plasmid pL32 was ligated to the ~1.6 kb SalI-XbaI restriction fragment of plasmid pCC101 in substantial accordance with the procedure of Example 2. The ligated DNA constituted the desired plasmid pL84. A restriction site and function map of plasmid pL84 is presented in FIG. 8 of the accompanying drawings. The ligated DNA was used to transform *E. coli* K12 MO(λ+) cells in substantial accordance with the procedure of Example 3. Plasmid pL84 DNA was prepared from the *E. coli* K12 MO(λ+)/pL84 transformants in substantial accordance with the procedure of Example 1.

EXAMPLE 9

Construction of *E. coli* K12 MO(λ+)/pL95

About 10 µg of plasmid pL84 were digested with about 50 units restriction enzyme NdeI in about 200 µl of high-salt buffer for two hours at 37° C. The NdeI-digested DNA was then precipitated and treated with Klenow in substantial accordance with the procedure of Example 5. The NdeI-digested, Klenow-treated plasmid pL84 DNA was then ligated to KpnI linkers (5'-GGGTACCC-3') in substantial accordance with the procedure of Example 2. After the linker ligation, the DNA was precipitated and the resulting DNA pellet was resuspended in 20 µl of 10X low-salt buffer (0.1M Tris-HCl, pH 7.6; 0.1M MgCl$_2$; and 10 mM DTT), 20 µl of 1 mg/ml BSA, 5 µl (about 50 units) restriction enzyme KpnI, and 155 µl of H$_2$O. The resulting reaction was incubated at 37° C. for two hours.

After the KpnI digestion, the DNA was loaded onto a low-melting-temperature agarose gel, and the ~3.8 kb restriction fragment was isolated and recircularized by ligation in substantial accordance with the procedure of Example 6. The ligated DNA constituted plasmid pL95, which was used to transform *E. coli* K12 MO(λ+) in substantial accordance with the procedure of Example 3. A restriction site and function map of plasmid pL95 is presented in FIG. 9 of the accompanying drawings.

EXAMPLE 10

Construction of *E. coli* K12 RV308/pPR12AR1

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 10 of the accompanying drawings.

About 10 µg of plasmid pPR12 were digested with about 50 units of restriction enzyme EcoRI in 200 µl of high-salt buffer at 37° C. for two hours. The EcoRI-digested plasmid pPR12 DNA was precipitated and treated with Klenow in substantial accordance with the procedure of Example 5. After the Klenow reaction, the EcoRI-digested, Klenow-treated plasmid pPR12 DNA was recircularized by ligation in substantial accordance with the procedure of Example 2. The ligated DNA, which constituted the desired plasmid pPR12ΔR1, was used to transform *E. coli* K12 RV308 in substantial accordance with the procedure of Example 3, except that selection was based on tetracycline (5 µg/ml) resistance, not ampicillin resistance. *E. coli* K12 RV308 is available from the NRRL under the accession number NRRL B-15624. After the *E. coli* K12 RV308/pPR12ΔR1 transformants were identified, plasmid pPR12ΔR1 DNA was prepared from the transformants in substantial accordance with the procedure of Example 1.

About 10 µg of plasmid pPR12ΔR1 were digested with about 50 units of restriction enzyme AvaI in 200 µl of medium-salt buffer at 37° C. for 2 hours. The AvaI-digested plasmid pPR12ΔR1 DNA was precipitated and treated with Klenow in substantial accordance with the procedure of Example 5. After the Klenow reaction, the AvaI-digested, Klenow-treated plasmid pPR12ΔR1 DNA was ligated to EcoR1 linkers (5'-GAGGAATTCCTC-3') in substantial accordance with the procedure of Example 2. After the linker ligation, the DNA was precipitated and then resuspended in about 200 μl of high-salt buffer containing about 50 units of restriction enzyme EcoR1. The resulting reaction was incubated at 37° C. for about 2 hours. After the EcoR1 digestion, the reaction mixture was loaded onto an agarose gel, and the ~5.1 kb EcoR1 restriction fragment was purified in substantial accordance with the procedure of Example 6. The ~5.1 kb EcoR1 restriction fragment was recircularized by ligation in substantial accordance with the procedure of Example 2. The ligated DNA constituted the desired plasmid pPR12AR1. The plasmid pPR12AR1 DNA was transformed into *E. coli* K12 RV308 in substantial accordance with the procedure of Example 3, except that selection was based on tetracycline resistance, not ampicillin resistance. After identifying the *E. coli* K12 RV308/pPR12AR1 transformants, plasmid pPR12AR1 DNA was prepared in substantial accordance with the procedure of Example 1. A restriction site and function map of plasmid pPR12AR1 is presented in FIG. 11 of the accompanying drawings.

EXAMPLE 11

Construction of *E. coli* K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoR1 restriction fragment of plasmid pPR12AR1 was isolated and prepared for ligation in substantial accordance with the procedure of Example 6.

About 10 μg of plasmid pL47 were digested with restriction enzymes PstI and BamHI in 200 μl of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 6. In a separate reaction, about 10 μg of plasmid pL47 DNA were digested with restriction enzymes EcoRI and BamHI in 200 μl of high-salt buffer at 37° C. for two hours, and the ~1.03 kb EcoRI-BamHI restriction fragment that comprised the novel transcriptional and translational activating sequence and the EK-BGH-encoding DNA was isolated and prepared for ligation in substantial accordance with the procedure of Example 6. The ~2 μg of the ~1.03 kb EcoRI-BamHI restriction fragment obtained were used in the construction of both plasmid pL110 and plasmid pL111. The construction of plasmid pL111 is described in Example 12.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 2 and 3, except that tetracycline resistance, not ampicillin resistance, was used as the basis for selecting transformants.

Two PstI restriction enzyme recognition sites are present in the EK-BGH coding region that are not depicted in the restriction site and function maps presented in the accompanying drawings. A restriction site and function map of plasmid pL110 is presented in FIG. 12 of the accompanying drawings.

EXAMPLE 12

Construction of *E. coli* K12 RV308/pL111

Plasmid pL111 was constructed in substantial accordance with the procedure of Example 11. The ~1.03 kb EcoRI-BamHI restriction fragment of plasmid pL47 was ligated to the ~2.03 kb BamHI-PstI restriction fragment of plasmid pL95 and to the ~2.9 kb PstI-EcoRI restriction fragment of plasmid pPR12AR1 to construct plasmid pL111, so plasmid pL111 differs from plasmid pL110 only in the sequences located downstream of the 3' end of the EK-BGH coding region. The ligation of the restriction fragments and the transformation of the resulting plasmid pL111 DNA into *E. coli* K12 RV308 was done in substantial accordance with the procedures of Examples 2 and 3, although tetracycline resistance, not ampicillin resistance, was used as the basis for selecting transformants. A restriction site and function map of plasmid pL111 is presented in FIG. 13 of the accompanying drawings.

EXAMPLE 13

Protocol for Induction of Functional Polypeptide Expression From the Lambda pL-lpp Hybrid Transcriptional and Translational Activating Sequence Although the following procedure specifically exemplifies induction of EK-BGH expression from the activating sequence of the present invention, the procedure is equally applicable to the induction of expression of other functional polypeptides using the expression vectors of the present invention.

The "cells" and "culture" referred to in the following procedure represent individual cultures of the following transformants of the present invention:

*E. coli* K12 RV308/pRK248cIts, pL47;
*E. coli* K12 RV308/pRK248cIts, pL84;
*E. coli* K12 RV308/pRK248cIts, pL95;
*E. coli* K12 RV308/pL110; and
*E. coli* K12 RV308/pL111.

Because *E. coli* K12 MO(λ+) comprises a wild-type lambda cI repressor gene, plasmids pL47, pL84, and pL95 had to be introduced into a host that comprised a temperature-sensitive lambda pL repressor gene to successfully conduct the induction experiments. Consequently, *E. coli* K12 RV308/pRK284cIts host cells were prepared and transformed with plasmids pL47, pL84, and pL95.

Plasmid pRK248cIts can be isolated from *E. coli* K12 JMB9/pRK248cIts, also known as *E. coli* K12 MCB3604, a strain deposited and made part of the permanent culture collection of the Northern Regional Research Laboratories. Plasmid pRK248cIts can be obtained from the NRRL under the accession number NRRL B-15631. Plasmid pRK248cIts comprises a temperature-sensitive mutant of the lambda pL repressor gene cI; the construction of plasmid pRK248cIts is described in Bernard and Helinski, 1979, Methods of Enzymology, 68:482, and Bernard et al., 1979, Gene 5:59. Plasmid pRK248cIts was isolated and purified in substantial accordance with the procedure of Example 1 and then transformed into *E. coli* K12 RV308 in substantial accordance with the procedure of Example 3. Because plasmid pRK248cIts comprises the tetracycline resistance-conferring gene, and not the ampicillin resistance-conferring gene, tetracycline resistance was used as the basis for selection of the *E. coli* K12 RV308/pRK248cIts transformants.

However, a variety of plasmids could be used in place of plasmid pRK248cIts for the purposes of this Example. Such plasmids would necessarily comprise a temperature-sensitive lambda pL repressor gene, a selectable marker independent of the ampicillin resistance-conferring gene, and a replicon, such as the replicon from plasmid pACYC184 or an R factor, that is compatible with the replicon of plasmid pBR322. Furthermore, temperature-sensitive control of the novel activating sequence of the present invention could also be obtained by using a host cell that comprised a chromosomally-integrated, temperature-sensitive cI repressor gene.

The *E. coli* K12 RV308/pRK248cIts transformants were made competent for transformation in substantial accordance with the procedure of Example 3, except that the *E. coli* K12 RV308/pRK248cIts culture was grown at 30° C. rather than 37° C., and the CaCl$_2$-treated cells were heat-shocked at 34° C. rather than 42° C. In separate transformations, plasmids pL47, pL84 and pL95 were transformed into the *E. coli* K12 RV308/pRK248cIts competent cells. Because the desired transformants comprise both the tetracycline resistance-conferring gene from plasmid pRK248cIts and also the ampicillin resistance-conferring gene from plasmid pL47, plasmid pL84, or plasmid pL95, both ampicillin and tetracycline selection were maintained to retain the plasmids in the transformants.

About 10 μl aliquots of cells at stationary phase were used to inoculate about 10 ml of LB media containing the appropriate antibiotic(s) for selection of cells containing the desired plasmid(s). The culture was incubated with shaking at 32° C. for about 16 hours. The culture was diluted with fresh media containing antibiotic(s) for plasmid selection so that the A$_{550}$ of the diluted culture was less than 0.1. The culture was incubated with shaking at 32° C. until the A$_{550}$ was ~0.3. Then, the culture was diluted 1:1 into fresh media, which had been warmed to 42° C. and contained antibiotics for plasmid selection, and incubation with shaking was continued at 42° C. for 2–4 hours.

One ml aliquots of the culture were removed at various points between two hours and four hours after the shift to 42° C. The cells were collected by centrifugation and resuspended in about 0.1 ml of sample buffer. Five ml of sample buffer are prepared by mixing into solution 1.8 g of urea, 2 mg bromophenol blue, 0.25 ml β-mercaptoethanol, 1.5 ml 10% SDS, 0.625 ml 4 X upper-Tris buffer (0.5M Tris-HCl, pH 6.8, and 0.4% SDS), and 0.75 ml glycerol. The samples were then boiled and electrophoresed on a 12% SDS-polyacrylamide gel. After Coomassie-Blue staining, the gel demonstrated that EK-BGH represented about 30% of the total cellular protein.

EXAMPLE 4

Construction of *E. coli* K12 RV308/pNM1093

About 10 μg of plasmid pL110 DNA is digested with about 50 units of restriction enzyme XbaI and about 2 units of restriction enzyme BamHI in 200 μl of high-salt buffer. The reaction is carried out so that the XbaI digest goes to near completion but the BamHI reaction is incomplete; the partial BamHI digest is necessary to isolate fragments that comprise the complete tetracycline resistance-conferring gene. The XbaI-BamHI-digested plasmid pL110 DNA is then loaded onto an agarose gel, and the ~6.0 kb XbaI-BamHI restriction fragment that comprises all of plasmid pL110 except the EK-BGH-encoding sequences is isolated and prepared for ligation in substantial accordance with the procedure of Example 6.

An ~0.6 kb XbaI-BamHI restriction fragment encoding MET-ASP-HGH is prepared and ligated to the ~6.0 kb XbaI-BamHI restriction fragment of plasmid pL110 to construct plasmid pNM1093. The sequence, numbered to facilitate discussion, of the ~0.6 kb XbaI-BamHI restriction fragment is depicted below:

```
                    10              20              30              40
5'-CTAGAGGGTATTAATA ATG GAT TTC CCA ACC ATT CCC TTA
   ||||||||||||||| ||| ||| ||| ||| ||| ||| ||| |||
3'-TCCCATAATTAT TAC CTA AAG GGT TGG TAA GGG AAT 50              60              70
TCC AGG CTT TTT GAC AAC GCT ATG CTC CGC GCC CAT CGT
||| ||| ||| ||| ||| ||| ||| ||| ||| ||| ||| ||| |||
AGG TCC GAA AAA CTG TTG CGA TAC GAG GCG CGG GTA GCA 80              90              100             110
CTG CAC CAG CTG GCC TTT GAC ACC TAC CAG GAG TTT GAA
||| ||| ||| ||| ||| ||| ||| ||| ||| ||| ||| ||| |||
GAC GTG GTC GAC CGG AAA CTG TGG ATG GTC CTC AAA CTT 120             130             140             150
GAA GCC TAT ATC CCA AAG GAA CAG AAG TAT TCA TTC CTG
||| ||| ||| ||| ||| ||| ||| ||| ||| ||| ||| ||| |||
CTT CGG ATA TAG GGT TTC CTT GTC TTC ATA AGT AAG GAC 160             170             180             190
CAG AAC CCC CAG ACC TCC CTC TGT TTC TCA GAG TCT ATT
||| ||| ||| ||| ||| ||| ||| ||| ||| ||| ||| ||| |||
GTC TTG GGG GTC TGG AGG GAG ACA AAG AGT CTC AGA TAA 200             210             220             230
CCG ACA CCC TCC AAC AGG GAG GAA ACA CAA CAG AAA TCC
||| ||| ||| ||| ||| ||| ||| ||| ||| ||| ||| ||| |||
GGC TGT GGG AGG TTG TCC CTC CTT TGT GTT GTC TTT AGG
```

```
          240           250           260           270
AAC CTA GAG CTG CTC CGC ATC TCC CTG CTG CTC ATC CAG
||| ||| ||| ||| ||| ||| ||| ||| ||| ||| ||| ||| |||
TTG GAT CTC GAC GAG GCG TAG AGG GAC GAC GAG TAG GTC 280           290           300           310
TCG TGG CTG GAG CCC GTG CAG TTC CTC AGG AGT GTC TTC
||| ||| ||| ||| ||| ||| ||| ||| ||| ||| ||| ||| |||
AGC ACC GAC CTC GGG CAC GTC AAG GAG TCC TCA CAG AAG 320           330           340           350
GCC AAC AGC CTG GTG TAC GGC GCC TCT GAC AGC AAC GTC
||| ||| ||| ||| ||| ||| ||| ||| ||| ||| ||| ||| |||
CGG TTG TCG GAC CAC ATG CCG CGG AGA CTG TCG TTG CAG 360           370           380           390
TAT GAC CTC CTA AAG GAC CTA GAG GAA GGC ATC CAA ACG
||| ||| ||| ||| ||| ||| ||| ||| ||| ||| ||| ||| |||
ATA CTG GAG GAT TTC CTG GAT CTC CTT CCG TAG GTT TGC 400           410           420           430
CTG ATG GGG AGG CTG GAA GAT GGC AGC CCC CGG ACT GGG
||| ||| ||| ||| ||| ||| ||| ||| ||| ||| ||| ||| |||
GAC TAC CCC TCC GAC CTT CTA CCG TCG GGG GCC TGA CCC 440           450           460
CAG ATC TTC AAG CAG ACC TAC AGC AAG TTC GAC ACA AAC
||| ||| ||| ||| ||| ||| ||| ||| ||| ||| ||| ||| |||
GTC TAG AAG TTC GTC TGG ATG TCG TTC AAG CTG TGT TTG 470       480           490           500
TCA CAC AAC GAT GAC GCA CTA CTC AAG AAC TAC GGG CTG
||| ||| ||| ||| ||| ||| ||| ||| ||| ||| ||| ||| |||
AGT GTG TTG CTA CTG CGT GAT GAG TTC TTG ATG CCC GAC 510       520           530           540
CTC TAC TGC TTC AGG AAG GAC ATG GAC AAG GTC GAG ACA
||| ||| ||| ||| ||| ||| ||| ||| ||| ||| ||| ||| |||
GAG ATG ACG AAG TCC TTC CTG TAC CTG TTC CAG CTC TGT 550       560           570           580
TTC CTG CGC ATC GTG CAG TGC CGC TCT GTG GAG GGC AGC
||| ||| ||| ||| ||| ||| ||| ||| ||| ||| ||| ||| |||
AAG GAC GCG TAG CAC GTC ACG GCG AGA CAC CTC CCG TCG 590           600
TGT GGC TTC TAG CTGCCCCCG-3'
||| ||| ||| ||| |||||||||
ACA CCG AAG ATC GACGGGGCCTAG-5'
```

The coding region for MET-ASP-HGH is located from nucleotide residue 17 to residue 595 in the sequence depicted above. The amino acid sequence of MET-ASP-HGH is depicted below, beginning with the residue at the amino terminus:

```
                    5                   10
          MET ASP PHE PRO THR ILE PRO LEU SER ARG LEU PHE ASP 15                  20                  25
          ASN ALA MET LEU ARG ALA HIS ARG LEU HIS GLN LEU ALA 30                  35
          PHE ASP THR TYR GLN GLU PHE GLU GLU ALA TYR ILE PRO 40                  45                  50
          LYS GLU GLN LYS TYR SER PHE LEU GLN ASN PRO GLN THR 55                  60                  65
          SER LEU CYS PHE SER GLU SER ILE PRO THR PRO SER ASN 70                  75
          ARG GLU GLU THR GLN GLN LYS SER ASN LEU GLU LEU LEU 80                  85                  90
          ARG ILE SER LEU LEU LEU ILE GLN SER TRP LEU GLU PRO 95                  100
          VAL GLN PHE LEU ARG SER VAL PHE ALA ASN SER LEU VAL
```

```
       105              110              115
TYR GLY ALA SER ASP SER ASN VAL TYR ASP LEU LEU LYS 120              125              130
ASP LEU GLU GLU GLY ILE GLN THR LEU MET GLY ARG LEU 135              140
GLU ASP GLY SER PRO ARG THR GLY GLN ILE PHE LYS GLN 145              150              155
THR TYR SER LYS PHE ASP THR ASN SER HIS ASN ASP ASP 160              165
ALA LEU LEU LYS ASN TYR GLY LEU LEU TYR CYS PHE ARG 170              175              180
LYS ASP MET ASP LYS VAL GLU THR PHE LEU ARG ILE VAL 185              190
GLN CYS ARG SER VAL GLU GLY SER CYS GLY PHE
```

The ~0.6 kb Xba-BamHI restriction fragment encoding MET-ASP-HGH can be prepared by synthetic means using procedures well-known in the art. Martial et al., 979, Science 205:602, have disclosed the cloning of much of the human growth hormone coding sequence by isolating human pituitary mRNA that comprised human growth hormone mRNA, preparing complementary DNA (cDNA) with reverse transcriptase, and inserting the cDNA into a plasmid vehicle. Goodman et al., 1979, Methods in Enzymology 68:75, have disclosed the procedure for isolating human pituitary mRNA. Furthermore, U.S. Pat. No. 4,363,877, issued Dec. 14, 1982 to Goodman et al., discloses that human growth hormone cDNA can be isolated from plasmid pHGH-1, which was deposited in the American Type Culture Collection, 12301 Parklawn Drive, Rockville, Md. 20852, under the accession number ATCC 40,000.

Human growth hormone cDNA can be used to prepare the ~0.6 kb XbaI-BamHI restriction fragment used in the construction of plasmid pNM1093. Once the cDNA has been cloned into a suitable plasmid vector, the ~0.6 kb XbaI-BamHI restriction fragment can be constructed by using restriction enzymes to isolate much of the human growth hormone coding sequence and then attaching synthetic DNA linkers designed to recreate the sequence of the ~0.6 kb XbaI-BamHI restriction fragment depicted above.

Plasmid pNM1093 was used to transform E. coli K12 RV308 in substantial accordance with the procedure of Example 3, except that tetracycline resistance, not ampicillin resistance, was used as the basis for selecting transformants. The E. coli K12 RV308/pNM1093 transformants express MET-ASP-HGH at levels approaching 30% of the total cellular protein when cultured in accordance with the procedure of Example 13.

I claim:

1. The lambda pL-Ipp hybrid transcriptional and translational activating sequence of the following structure:

```
           10         20         30
5'-GATCTCTCAC CTACCAAACA ATGCCCCCCT
   |||||||||| |||||||||| ||||||||||
3'-CTAGAGAGTG GATGGTTTGT TACGGGGGGA 40         50         60
   GCAAAAAATA AATTCATATA AAAACATAC
   |||||||||| |||||||||| |||||||||
   CGTTTTTTAT TTAAGTATAT TTTTTGTATG 70         80         90
   AGATAACCAT CTGCGGTGAT AAATTATCTC
   |||||||||| |||||||||| ||||||||||
   TCTATTGGTA GACGCCACTA TTTAATAGAG 100        110        120
   TGGCGGTGTT GACATAAATA CCACTGGCGG
   |||||||||| |||||||||| ||||||||||
   ACCGCCACAA CTGTATTTAT GGTGACCGCC 130        140        150
   TGATACTGAG CACATCAGAT CTATTAACTC
   |||||||||| |||||||||| ||||||||||
   ACTATGACTC GTGTAGTCTA GATAATTGAG 160        170
   AATCTAGAGG GTATTAATAA TG—3'
   |||||||||| |||||||||| ||
   TTAGATCTCC CATAATTATT AC—5'
``` wherein

A is deoxyadenyl;

G is deoxyguanyl;

C is deoxycytidyl; and

T is thymidyl.

2. A recombinant DNA expression vector that comprises the sequence of claim 1.

3. The recombinant DNA expression vector of claim 2 which is a plasmid.

4. The plasmid of claim 3 that further comprises the following elements:

a. a rop⁻ replicon derived from plasmid pBR322;

b. a selectable marker; and c. a DNA sequence that encodes a functional polypeptide.

5. The plasmid of claim 4 that is plasmid pL47.

6. The plasmid of claim 4 that is plasmid pL84.

7. The plasmid of Claim 4 that is plasmid pL95.

8. The plasmid of claim 4 that further comprises a gene that encodes a temperature-sensitive cI repressor of lambda pL.

9. The plasmid of claim 8 wherein the selectable marker is the tetracycline resistance-conferring gene, the gene that encodes a temperature-sensitive repressor of lambda pL is cI857, and the DNA sequence that encodes a functional polypeptide is a DNA sequence that encodes EK-BGH.

10. The plasmid of claim 8 wherein the selectable marker is the tetracycline resistance-conferring gene, the gene that encodes a temperature-sensitive repressor of lambda pL is cI857, and the DNA sequence that encodes a functional polypeptide is a DNA sequence that encodes MET-ASP-HGH.

11. The plasmid of claim 9 that is plasmid pL110.
12. The plasmid of claim 9 that is plasmid pL111.
13. The plasmid of claim 10 that is plasmid pNM1093.
14. A host cell transformed with an expression vector of claim 2.
15. A host cell transformed with a plasmid of claim 3.
16. A host cell transformed with a plasmid of claim 4.
17. The host cell of claim 16 that is E. coli K12 RV308/pRK248cIts, pL47.
18. The host cell of claim 16 that is E. coli K12 RV308/pRK248cIts, pL84.
19. The host cell of claim 16 that is E. coli K12 RV308/pRK248cIts, pL95.
20. A host cell transformed with a plasmid of claim 8.
21. The host cell of claim 20 that is E. coli K12 RV308/pL110.
22. The host cell of claim 20 that is E. coli K12 RV308/pL111.
23. The host cell of claim 20 that is E. coli K12 RV308/pNM1093.
24. A plasmid selected from the group consisting of plasmids pKC283PX, pKC283-L, pKC283-LB, pL32, pKC283PRS, pPR12ΔR1 and pPR12AR1.

* * * * *

UNITED STATES PATENT AND TRADEMARK OFFICE
CERTIFICATE OF CORRECTION

PATENT NO. : 4,874,703
DATED : October 17, 1989
INVENTOR(S) : S. Richard Jaskunas It is certified that error appears in the above-identified patent and that said Letters Patent is hereby corrected as shown below:

In column 3, line 18, change "funct" to -- function --.

In column 4, line 27, change "activating but" to -- activating sequence but --.

In column 5, line 13, change "aspartylhuman" to -- aspartyl-human --.

In column 6, line 20, change "expression-on" to -- expression --.

In column 9, line 41, change "MET-SP" to -- MET-ASP --.

In column 11, line 65, change "(λ-)" to -- (λ+) --.

In column 15, line 53, change "~1" to -- µl --.

In column 20, line 20, change "EXAMPLE 4" to -- EXAMPLE 14 --.

Signed and Sealed this

Seventeenth Day of May, 1994

BRUCE LEHMAN

*Attest:*

*Attesting Officer*      *Commissioner of Patents and Trademarks*